United States Patent
Kim et al.

(10) Patent No.: US 12,409,254 B2
(45) Date of Patent: Sep. 9, 2025

(54) CATHETER INSERT DEVICES

(71) Applicant: THE REGENTS OF THE UNIVERSITY OF MICHIGAN, Ann Arbor, MI (US)

(72) Inventors: Maria Kim, Ann Arbor, MI (US); Elizabeth J. Brisbois, Athens, GA (US); Joshua C. Doverspike, Ann Arbor, MI (US); Shale J. Mack, Ann Arbor, MI (US); Orsolya I. Lautner-Csorba, Ann Arbor, MI (US); Kamila Katarzyna Konopinska, Vista, CA (US); Mark E. Meyerhoff, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 886 days.

(21) Appl. No.: 17/617,507

(22) PCT Filed: Jun. 9, 2020

(86) PCT No.: PCT/US2020/036823
§ 371 (c)(1),
(2) Date: Dec. 8, 2021

(87) PCT Pub. No.: WO2020/251947
PCT Pub. Date: Dec. 17, 2020

(65) Prior Publication Data
US 2022/0218880 A1  Jul. 14, 2022

Related U.S. Application Data

(60) Provisional application No. 62/859,515, filed on Jun. 10, 2019.

(51) Int. Cl.
*A61L 29/16* (2006.01)
*A61L 29/02* (2006.01)
(Continued)

(52) U.S. Cl.
CPC ............... *A61L 29/16* (2013.01); *A61L 29/02* (2013.01); *A61L 29/06* (2013.01);
(Continued)

(58) Field of Classification Search
CPC .. A61M 2025/0065; A61M 2025/0057; A61M 2202/0275; A61L 2300/114
See application file for complete search history.

(56) References Cited

U.S. PATENT DOCUMENTS 6,602,241 B2   8/2003   Makower et al.
8,981,139 B2   3/2015   Schoenfisch et al.
(Continued)

FOREIGN PATENT DOCUMENTS

CN   102065848 A   5/2011
CN   105307695 A   2/2016
(Continued)

OTHER PUBLICATIONS

Brisbois et al., "Improved Hemocompatability of Multilumen Catheters via Nitric Oxide (NO) Release from S-Nitroso-N-acetylpenicillamine (SNAP) Composite Filled Lumen", ACS Applied Materials and Interfaces, Oct. 13, 2016, 8, pp. 29272-29279. (Year: 2016).*

(Continued)

*Primary Examiner* — Laura A Bouchelle
(74) *Attorney, Agent, or Firm* — Dierker & Kavanaugh, P.C.

(57) ABSTRACT

A catheter insert device includes a powder composition, and a housing. The powder composition includes a solid phase S-nitrosothiol (RSNO). The housing includes a polymeric wall that is i) permeable to nitric oxide, ii) non-porous, and iii) permeable to water vapor, and an inner lumen defined at least in part by the polymeric wall. The powder composition is completely sealed within the inner lumen of the housing.

26 Claims, 21 Drawing Sheets

(51) Int. Cl.
*A61L 29/06* (2006.01)
*A61M 25/00* (2006.01)

(52) U.S. Cl.
CPC .... *A61M 25/0043* (2013.01); *A61L 2300/114* (2013.01); *A61L 2300/60* (2013.01); *A61M 2025/0056* (2013.01)

(56) References Cited

U.S. PATENT DOCUMENTS

| | | | |
|---|---|---|---|
| 10,709,360 B2 * | 7/2020 | Chen | A61B 5/6852 |
| 2002/0098278 A1 | 7/2002 | Bates et al. | |
| 2006/0058737 A1 | 3/2006 | Herweck et al. | |
| 2010/0098733 A1 | 4/2010 | Stasko | |
| 2010/0106102 A1 | 4/2010 | Ziebol et al. | |
| 2010/0106103 A1 | 4/2010 | Ziebol et al. | |
| 2010/0174245 A1 | 7/2010 | Halverson et al. | |
| 2013/0144258 A1 | 6/2013 | Ziebol et al. | |
| 2013/0184679 A1 | 7/2013 | Ziebol et al. | |
| 2013/0204231 A1 | 8/2013 | Ziebol et al. | |
| 2013/0274686 A1 | 10/2013 | Ziebol et al. | |
| 2015/0343174 A1 | 12/2015 | Ziebol et al. | |
| 2015/0366831 A1 | 12/2015 | Brisbois et al. | |
| 2016/0001058 A1 | 1/2016 | Ziebol et al. | |
| 2019/0039910 A1 | 2/2019 | Handa et al. | |

FOREIGN PATENT DOCUMENTS

| | | | | |
|---|---|---|---|---|
| CN | 104194460 A | | 5/2016 | |
| CN | 109069701 A | | 12/2018 | |
| WO | 2002056864 A2 | | 7/2002 | |
| WO | 2002056904 A1 | | 7/2002 | |
| WO | 2007064895 A2 | | 6/2007 | |
| WO | WO 2008/153762 | | 12/2008 | |
| WO | 2010044875 A2 | | 4/2010 | |
| WO | WO-2017147295 A1 * | 8/2017 | ........... A61K 31/095 |
| WO | 2018136845 A1 | | 7/2018 | |

OTHER PUBLICATIONS

Brisbois et al., Improved Hemocompatability of Multilumen Catheters via Nitric Oxide (NO) Release from S-Nitroso-N-acetylpenicillamine (SNAP) Composite Filled Lumen, ACS Applied Materials and Interfaces, Oct. 13, 2016, 8, pp. 29270-29279.

Pant et al., "Tunable Nitric Oxide Release from S-Nitroso-N-acetylpenicillamine via Catalytic Copper Nanoparticles for Biomedical Applications", ACS Applied Materials and Interfaces, Apr. 14, 2017, 9 (18), pp. 15254-15264.

Hymes et al., "Dialysis Catheter-Related Bloodstream Infections: A Cluster-Randomized Trial of the ClearGuard HD Antimicrobial Barrier Cap", American Journal of Kidney Diseases, vol. 69, No. 2, 2017, pp. 220-227, DOI: 1 0.1053/J.AJKD.2016.09.014, Nov. 10, 2016.

* cited by examiner

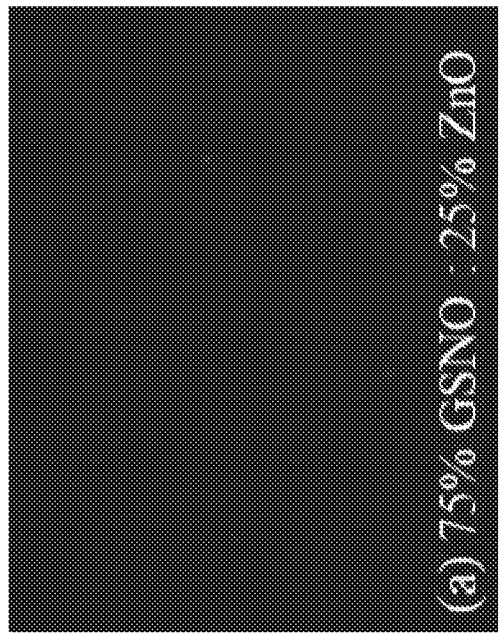
FIG. 17A Control (no insert)
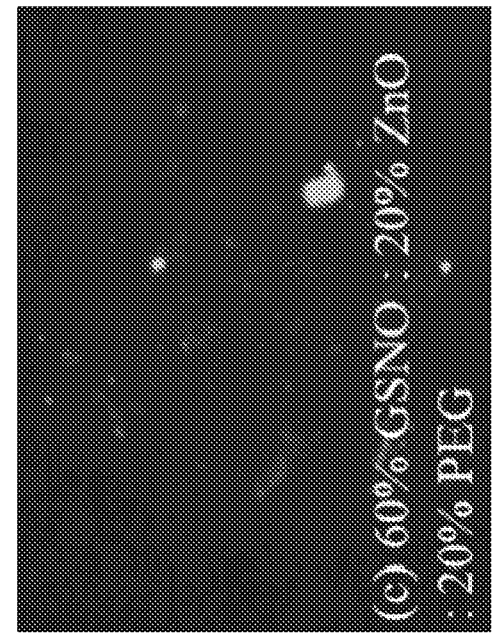
FIG. 17B (a) 75% GSNO : 25% ZnO
FIG. 17C (b) 25% GSNO : 75% ZnO
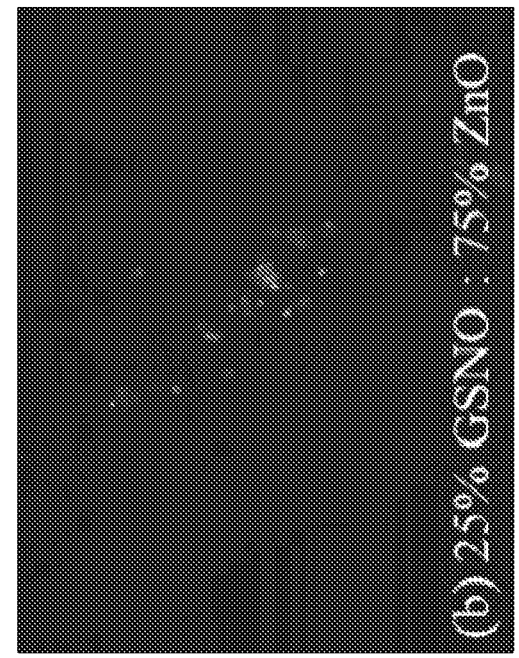
FIG. 17D (c) 60% GSNO : 20% ZnO : 20% PEG

CATHETER INSERT DEVICES

CROSS-REFERENCE TO RELATED APPLICATIONS

This application claims the benefit of U.S. provisional application Ser. No. 62/859,515, filed Jun. 10, 2019, the contents of which is incorporated by reference herein in its entirety.

STATEMENT REGARDING FEDERALLY SPONSORED RESEARCH OR DEVELOPMENT

This invention was made with government support under HL128337 awarded by the National Institutes of Health. The government has certain rights in the invention.

BACKGROUND

Catheters are medical devices that can be inserted into the human body, for example, via a body cavity, duct, or vessel. Catheters may be used in a variety of medical applications because they serve a broad range of functions. Example applications in which catheters may be used include cardiovascular, urological, gastrointestinal, neurovascular, and ophthalmic applications. Catheter functions range anywhere from fluid drainage, to fluid or gas administration, to enabling access by surgical instruments, to enabling other tasks depending upon the type of catheter. Catheters can be designed and manufactured as temporary catheters or permanent catheters. Acute catheters are one example of temporary catheters, as they are suitable for short term use (e.g., up to 7 days). Acute catheters are often used in operating rooms, emergency rooms, and intensive care units. Chronic catheters are another example of temporary catheters, as they are suitable for relatively short term use (e.g., 7 to 30 days). Chronic catheters are often used for parenteral nutrition, drug infusion, and dialysis. Permanent catheters are for long term use (e.g., months to years), and may be used, for example, for long-term nutrition and pacemaker leads.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 17A through 17D are fluorescent microscopy images of *S. Aureus* bacteria/biofilm adhered to the inner lumen wall of a simulated hub after exposure to no insert device and three example catheter insert devices;

FIGS. 29A and 28B are black and white reproductions of originally colored fluorescent microscopy images depicting a distal intravascular region of a control catheter catheter (in comp. sheep 3) that was not treated with an insert device (FIG. 29A) and of an example catheter (in example sheep 4) that was treated with an insert device (FIG. 29B), where green staining depicted live bacteria and red (not readily visible) depicted dead bacteria;

FIGS. 35A and 35B are black and white reproductions of originally colored fluorescent microscopy images depicting a distal tip of a comparative catheter that was treated with a comparative device cap (FIG. 35A) and of an example catheter that was treated with an example insert device (FIG. 35B), where green staining depicted live bacteria and red (not readily visible) depicted dead bacteria.

DETAILED DESCRIPTION

Disclosed herein is a catheter insert device that is capable of selectively generating nitric oxide (NO) when inserted at least partially into a catheter containing a lock solution. A lock solution is introduced into a catheter when it is not in use for its designated medical application (e.g., therapeutic infusion, fluid extraction, etc.). A lock solution is primarily used to ensure a blood-solution interface is present at the distal tip of the catheter, and in some instances, is also used to prevent clotting.

The catheter insert device disclosed herein includes at least a solid phase nitric oxide donor. The donor is completely sealed within an inner lumen of a non-porous housing, so that the solid phase component cannot leach (leak, diffuse, etc.) out of the insert device. However, the non-porous housing is also permeable to both water vapor and NO. When the insert device is in contact with the lock solution, water vapor can permeate through the housing into the inner lumen, where it hydrates the solid phase nitric oxide donor contained therein. This initiates the decomposition of the solid phase nitric oxide donor, which liberates NO. The NO can permeate through the insert housing into the catheter. As such, in the examples disclosed herein, the catheter insert device does not contain the therapeutic agent that is to be delivered to the catheter, but rather generates the therapeutic agent (nitric oxide) over an extended time period when it is inserted into the catheter containing the lock solution. This is unlike other catheter disinfectant devices, which directly deliver an antimicrobial or antibiotic or other therapeutic agent into the catheter.

NO has several important physiological functions, including anti-microbial/anti-viral activity. The NO produced and released into the catheter can reduce bacterial load on the interior walls of the catheter, and thus may act as is disinfectant. The NO may also be able to prevent bacteria adhesion and biofilm formation on the interior catheter walls. Moreover, the levels of NO produced may be ample enough to enable NO diffusion through the outer walls of the catheter. The NO at the exterior of the catheter can have an anti-microbial and/or therapeutic effect, for example, to control infection, to minimize inflammation and fibrosis, to inhibit local platelet activity, clotting, and/or thrombus formation, to help kill bacteria and viruses, to disrupt bacterial biofilm formation, and to disperse or prevent microbial biofilm formation (e.g., disperse antibiotic resistant biofilms). These effects may significantly reduce the risk of infection that is often associated with catheters.

Figure 1:
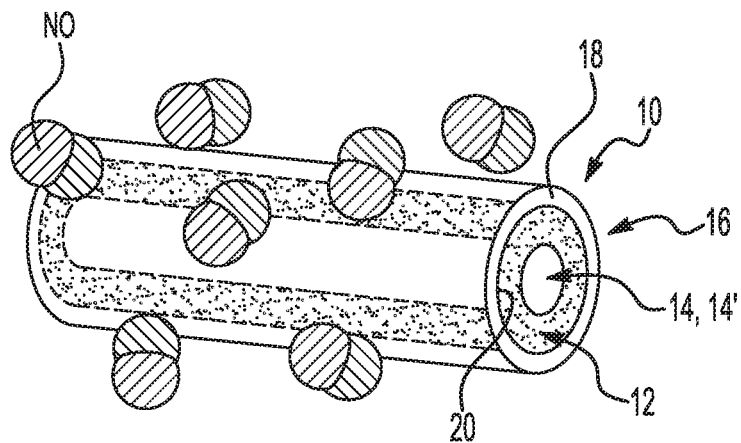
FIG. 1 is a perspective, schematic view of an example of a catheter insert device without its opposed ends completely sealed.

An example of the catheter insert device is shown in FIG. 1. The catheter insert device 10 includes a powder composition 12 including a solid phase S-nitrosothiol (RSNO); a housing 16, including a polymeric wall 18 that is i) permeable to nitric oxide, ii) non-porous, and iii) permeable to water vapor; and an inner lumen 20 defined at least in part by the polymeric wall 18, wherein the powder composition 12 is completely sealed within the inner lumen 20 of the housing 16.

In some examples, the device 10 further includes a solid phase additive 14 to accelerate the rate of release of nitric oxide from the solid phase RSNO after exposure to water vapor, where the solid phase additive 14 is also completely sealed within the inner lumen of the housing. Generally, the solid phase additive 14 is selected from the group consisting of zinc oxide nanoparticles, a copper (II/I)-ligand complex, a metal wire, metal nanoparticles, ascorbic acid, a thiol, a hydrogen ion precursor, a selenium species, an organo-selenium molecule, an organo-tellurium molecule, silica or polymeric particles coated with or possessing immobilized forms of an organic accelerant species, and combinations thereof. As will be described in further details herein, the solid phase additive 14 may be a component of the powder composition 12 or may be incorporated into the device 10 as a separate component (e.g., a metal wire 14').

The powder composition 12 includes at least the solid phase nitric oxide donor. In the examples disclosed herein, the solid phase nitric oxide donor is a solid phase S-nitrosothiol (RSNO). This means that the RSNO is in solid form, e.g., as powder, nanoparticles, etc. Some specific examples of S-nitrosothiols are selected from the group consisting of S-nitrosoglutathione (GSNO, naturally occurring in the human body), S-nitroso-cysteine (CYSNO, naturally occurring in the human body), S-nitroso-N-acetyl-penicillamine (SNAP, decomposes to the drug, penicillamine), S-nitroso-penicillamine, S-nitroso-human serum albumin (naturally occurring in the human body), and combinations thereof.

In some instances, the powder composition 12 includes 100% (by weight) of the solid phase RSNO. In these examples, the powder composition 12 consists of the solid phase RSNO, with no other components.

In other instances, the powder composition 12 includes the solid phase S-nitrosothiol and the solid phase additive 14 (also referred to herein as the solid phase accelerant). In these examples, the solid phase additive 14 is part of the powder composition 12; and the solid phase additive 14 is selected from the group consisting of zinc oxide nanoparticles, a copper (II/I)-ligand complex, copper nanoparticles, ascorbic acid, a thiol, a hydrogen ion precursor, a selenium species, an organo-selenium molecule, an organo-tellurium molecule, stainless steel nanoparticles, gold nanoparticles, silica or polymeric particles coated with or possessing immobilized forms of an organic accelerant species, and combinations thereof. In these examples, the powder composition 12 includes (or consists of) from about 15 wt % to about 95 wt % of the solid phase RSNO and from about 5 wt % to about 85 wt % of the solid phase additive 14. In other examples, the powder composition 12 includes (or consists of) from about 75 wt % to about 95 wt % of the solid phase RSNO and from about 5 wt % to about 30 wt % of the solid phase additive 14. As one example, the powder composition 12 includes about 75 wt % GSNO and 25 wt % ZnO nanoparticles. Examples of the powder composition 12 with lower amounts of the solid phase RSNO release less NO and release NO for a shorter time period than examples of the powder composition 12 with higher amounts of the solid phase RSNO. Lower amounts of the solid phase RSNO may be desirable, for example, when the insert device 10 is changed frequently.

Any of the nanoparticles that may be used as the solid phase additives 14 may have a particle size (e.g., volume-weighted mean diameter) ranging from about 1 nm to about 900 nm. For example, the zinc oxide, copper, stainless steel, or gold nanoparticles may have a particle size ranging from about 5 nm to about 800 nm.

A copper (II)-ligand complex or a copper (I)-ligand complex may be used as the solid phase additive 14. Examples of suitable copper (II/I)-ligand complexes that may be used as the solid phase additives 14 include Cu(II)-ligand complexes that are selected from the group consisting of Cu(II)-tri(2-pyridylmethyl)amine (CuTPMA), Cu(II)-tris [2-(dimethylamino)ethyl]amine (CuMe$_6$Tren), Cu(II)-tri(2-pyridylmethyl)phosphine (CuTPMP), Cu(II)-1,4,7-trimethyl-1,4-7-triazacyclononane (Cu(Me$_3$TACN)), Cu(II)-1,4,7-triethyl-1,4-7-triazacyclononane (Cu(Et$_3$TACN)), Cu(II)-1,4,7-tripropyl-1,4-7-triazacyclononane (Cu(Pr$_3$TACN)), Cu(II)-1,4,7-triisopropyl-1,4-7-triazacyclononane (Cu(iPr$_3$TACN)), Cu(II)-(N,N-bis-(2-pyridylmethyl)amine-N-ethylate) (Cu(BMPA-Et)), Cu(II)-(N,N-bis-(2-pyridylmethyl)amine-N-propanoate) (Cu(BMPA-Pr)), Cu(II)-(N,N-bis-(2-pyridylmethyl)amine-N-butylate) (Cu(BMPA-Bu)), Cu(II)-(N,N-bis-(2-pyridylethyl)amine-N-ethylate) (Cu(BEPA-Et)), Cu(II)-(N,N-bis-(2-pyridylethyl)amine-N-propanoate) (Cu(BEPA-Pr)), Cu(II)-(N,N-bis-(2-pyridylethyl)amine-N-butylate (Cu(BEPA-Bu)), Cu(II)-(N,N-bis-(2-pyridylmethyl)amine-N-methyl-phenolate) (Cu(BMPA-MePhO)), Cu(II)-(N,N-bis-(2-pyridylmethyl)amine-N-ethyl-phenolate) (Cu(BMPA-EtPhO)), Cu(II)-(N,N-bis-(2-pyridylmethyl)amine-N-propyl-phenolate) (Cu(BMPA-PrPhO)), Cu(II)-(N,N-bis-(2-pyridylethyl)amine-N-methyl-phenolate) (Cu(BEPA-MePhO)), Cu(II)-(N,N-bis-(2-pyridylethyl)amine-N-ethyl-phenolate) (Cu(BEPA-EtPhO)), Cu(II)-(N,N-bis-(2-pyridylethyl)amine-N-propyl-phenolate) (Cu(BEPA-PrPhO)), Cu(II)-3-((2-(pyridin-2-yl)ethyl)(pyridin-2-ylmethyl)amino)ethylate (Cu(PEMA-Et)), Cu(II)-3-((2-(pyridin-2-yl)ethyl)(pyridin-2-ylmethyl)amino)propanoate (Cu(PEMA-Pr)), Cu(II)-3-((2-(pyridin-2-yl)ethyl)(pyridin-2-ylmethyl)amino)butylate (Cu(PEMA-Bu)), Cu(II)-2-(pyridin-2-yl)-N,N-bis(pyridin-2-ylmethyl)ethan-1-amine (Cu(PMEA)), Cu(II)-2,2'-(2-(2-(pyridin-2-yl)ethyl)butane-1,4-diyl)dipyridine (Cu(PMAP)), and combinations thereof. In a specific example, the Cu(II)-ligand complex may be selected from Cu(II)-tri(2-pyridylmethyl)amine (CuTPMA), Cu(II)-tris[2-(dimethylamino)ethyl]amine (CuMe$_6$Tren), Cu(II)-tri(2-pyridylmethyl)phosphine (CuTPMP), and combinations thereof. While several examples of the Cu(II)-ligand complex are provided herein, it is to be understood that other water soluble Cu(II)-complexes or Cu(I) complexes may be used. The copper (I) complex should be stable so that it does not immediately react with oxygen and form Cu(II).

Examples of suitable thiols that may be used as the solid phase additive 14 include glutathione and cysteine.

Examples of hydrogen ion precursors that may be used as the solid phase additive 14 include any acids that can generate a hydrogen ion (proton), such as poly(lactic-co-glycolic acid).

An example of a suitable selenium species that may be used as the solid phase additive 14 includes selenocystamine. Another suitable organo-selenium molecule includes glutathione peroxidase, which has selenocystamine within its structure. Examples of suitable organo-tellurium molecules include 5,5'-ditelluro-2,2'-dithuophenecarboxylic acid and other similar di-tellurium species.

The stainless steel nanoparticles may be any suitable grade, such as stainless steel type 316, 316L, 317, or the like. While some metal nanoparticles are listed, it is to be understood that other metal nanoparticles may be used, as long as they act as a trigger and/or catalyst for the decomposition of the RSNO.

Any of the organic accelerant species (e.g., copper (II/I)-ligand complexes, organo-selenium molecules, organo-tellurium molecules, etc.) may also be immobilized or coated on the surface of solid phase particles, such as silica, gold, polystyrene, or other or polymeric particles (e.g., polyurethane particles). These coated particles may be used as the solid phase accelerant/additive 14 (e.g., in the powder composition 12).

In the examples disclosed herein, the solid phase accelerant/additive 14 can trigger and/or catalyze the decomposition of the nitric oxide donor into nitric oxide. The following are some examples of how the solid phase accelerant/additive 14 can control or accelerate the rate of release of nitric oxide, in particular, from GSNO. In one example, when the zinc oxide nanoparticles are heated to physiological temperature, the polarization density decreases ($\Delta Ps<0$) causing uncompensated charges (both positive and negative) on the surface. It is believed that the negative charges reduce the GSNO to produce NO and GSH (i.e., glutathione). After GSH is produced, the positive charge on the zinc oxide surface is able to oxidize the GSH to form GS·. Then, two GS· can combine to form the disulfide GSSG. In another example, glutathione can increase the NO release rate from GSNO via the formation of an initial N-hydroxysulfenamide species (e.g., GS-N(OH)-SG), which then converts to a radical GS· that can react with another GSNO molecule to liberate NO and form the GSSG disulfide species. In still another example, ascorbic acid or ascorbate can readily oxidize to form smaller threose structures (3 carbon sugars). The spontaneous oxidation of ascorbate can be coupled with reduction of GSNO to liberate NO plus GSH. Further, the oxidation products of ascorbate, i.e., the smaller threose structures, are also reducing agents that can provide electron (s) to GSNO, and thus may also contribute to the direct reduction of the GSNO to NO. In an example, the ascorbic acid or ascorbate may be allowed to oxidize in a solution for up to 5 days, dried, and then incorporated as part of the solid phase insert powder composition 12. An organoselenium species can catalyze NO generation from GSNO. Copper ions (from copper particles, a copper layer, or copper (II/I) complexes) may be reduced to their +1 oxidation state by any trace free thiols that exist in the formulation, and the Cu(I) ions can then reduce the GSNO to NO and GSH. In any of these examples, the products and by-products from the RSNO remain in the sealed housing 16, except for the nitric oxide, which can permeate through the polymeric wall(s) 18.

In still other instances, the powder composition 12 includes the solid phase S-nitrosothiol and a water uptake material. The water uptake material is capable of enhancing the water uptake into the lumen 20 of the insert device 10. The addition of the water uptake material should increase the internal viscosity upon moisture absorption, which, when used with GSNO may impose a cage effect on the thiyl and NO radical pair, such that they recombine to form GSNO and slow the rate of NO release. The water uptake material may be any polymer or chemical that has a water uptake of at least 0.5 wt %. The water uptake may be calculated by the following equation:

$$\text{water uptake } (wt\%) = (W_{wet} - W_{dry})/W_{dry} \times 100 \qquad \text{(Eq. 1)}$$

where $W_{wet}$ and $W_{dry}$ are the weights of the wet and dry water uptake material, respectively. Examples of suitable water uptake materials are selected from the group consisting of poly(ethylene glycol) (PEG), poly(vinyl alcohol) (PVA), a polypeptide, a polyionic species, a monosaccharide, a polysaccharide, silica particles, and a salt. Proteins may also be used as water uptake materials. Examples of suitable polyionic species include heparin, chondroitin sulfate, polyphosphates, polyquaternary ammonium species, etc. The poly(ethylene glycol) (PEG) may have a weight average molecular weight ranging from about 1,000 g/mol to about 50,000 g/mol. In an example, the poly(ethylene glycol) has a weight average molecular weight of about 4,000 g/mol (or Daltons). An example of a suitable monosaccharide is glucose. Examples of suitable polysaccharides include sucrose, amylose starch, etc. Examples of suitable salts include any that can increase osmolarity with the insert device 10 to draw up water, such as sodium chloride (NaCl), potassium chloride (KCl), etc.

In these examples, a weight ratio of the solid phase RSNO to the water uptake material ranges from 1:1 to 19:1. In some examples, the powder composition 12 consists of from about 50 wt % to about 90 wt % of the solid phase RSNO and from about 9 wt % to about 50 wt % of the water uptake material. In other examples, the powder composition 12 consists of from about 70 wt % to about 95 wt % of the solid phase RSNO and from about 5 wt % to about 30 wt % of the water uptake material. As one example, the powder composition 12 includes about 80 wt % SNAP and 20 wt % solid PEG particles (MW=4,000 g/mol) (weight ratio=4:1).

In other examples, the powder composition 12 includes the solid phase RSNO, the solid phase additive 14, and the water uptake material. In these examples, a weight ratio of the solid phase RSNO to the water uptake material ranges from 1:1 to 10:1. In some of these examples, the powder composition 12 consists of from about 40 wt % to about 85.5 wt % of the solid phase RSNO, from about 5 wt % to about 20 wt % of the solid phase additive 14, and from about 8 wt % to about 47.5 wt % of the water uptake material.

When the powder composition 12 includes the solid phase RSNO alone or in combination with the water uptake material, the device 10 may further comprises a solid phase additive completely sealed within the inner lumen of the housing, wherein the solid phase additive is a metal wire 14'. In one example, the separate solid phase additive, i.e., metal wire 14' is a stainless steel wire or a copper wire. While some metal wires are listed, it is to be understood that other metal wires that can trigger and/or catalyze the decomposition of the nitric oxide donor (the solid phase RSNO) into nitric oxide may be used.

The length of the metal wire 14' may depend, in part, upon the dimensions of the inner lumen 20 of the housing 16. In some examples, the metal wire 14' may extend through the entire length of the inner lumen 20, and in other example, the metal wire 14' may extend partially through the length of the inner lumen 20. The width or diameter of the metal wire 14' is smaller than the width or diameter of the inner lumen 20 so that the inner lumen 20 can accommodate both the metal wire 14' and the powder composition 12. In an example, the metal wire 14' has a diameter (outer diameter) of about 0.3 mm.

The metal wire 14' may be introduced into the housing 16 along with the powder composition 12 (which includes the solid phase RSNO, and may or may not include another solid phase additive 14 and/or the water uptake material). The example shown in FIG. 1 includes one metal wire 14' in the housing 16 and surrounded by the powder composition 12.

It is to be understood that the separate solid phase additive (e.g., the metal wire 14') may also be used with any example of the powder composition 12 disclosed herein. For example, the powder composition 12 may include the solid phase RSNO, optionally the water uptake material, and optionally another solid phase additive 14 (e.g., any of the particle forms disclosed herein).

The housing 16 includes a polymeric wall 18 that is i) permeable to nitric oxide, ii) non-porous, and iii) permeable to water vapor; and an inner lumen 20 defined at least in part by the polymeric wall 18. The polymeric wall may be any polymeric tubing material that has these characteristics. The permeability to water vapor may be relatively low, for example, the water uptake may be as low as 0.9 wt %. Examples of non-porous, NO permeable, and water vapor permeable polymeric materials that may be used for the polymeric wall(s) 18 of the housing 16 may be selected from the group consisting of silicone rubber, polyurethane, polyethylene, plasticized poly(vinyl chloride) (PVC), siloxane-based polyurethane elastomers, and thermoplastic silicone-polycarbonate-polyurethane. In one example, silicone rubber tubing may be desirable because of the high diffusivity of NO through silicone rubber compared to other biomedical grade polymers and because the relatively low hardness of silicone rubber allows moisture to pass through its walls to initiate NO release from the solid phase RSNO.

The housing 16 may be formed of a single piece of the polymeric material that is filled with the powder composition 12 and is sealed by an adhesive or other sealing mechanism. The housing 16 may also be a tube (as shown in FIG. 1) that is sealed at the opposed ends with leak-proof sealing members. For example, the polymeric wall 18 is an insert tube, and the housing 16 further comprises respective sealing mechanisms attached to opposed ends of the insert tube. Example sealing mechanisms include polyethylene or polypropylene or some other hard plastic plugs, or a plug made of the same plastic as the insert tubing. The plugs may be solvent sealed in place at the ends. Other sealing mechanisms may include conventional silicone caulking type materials.

Figure 2:
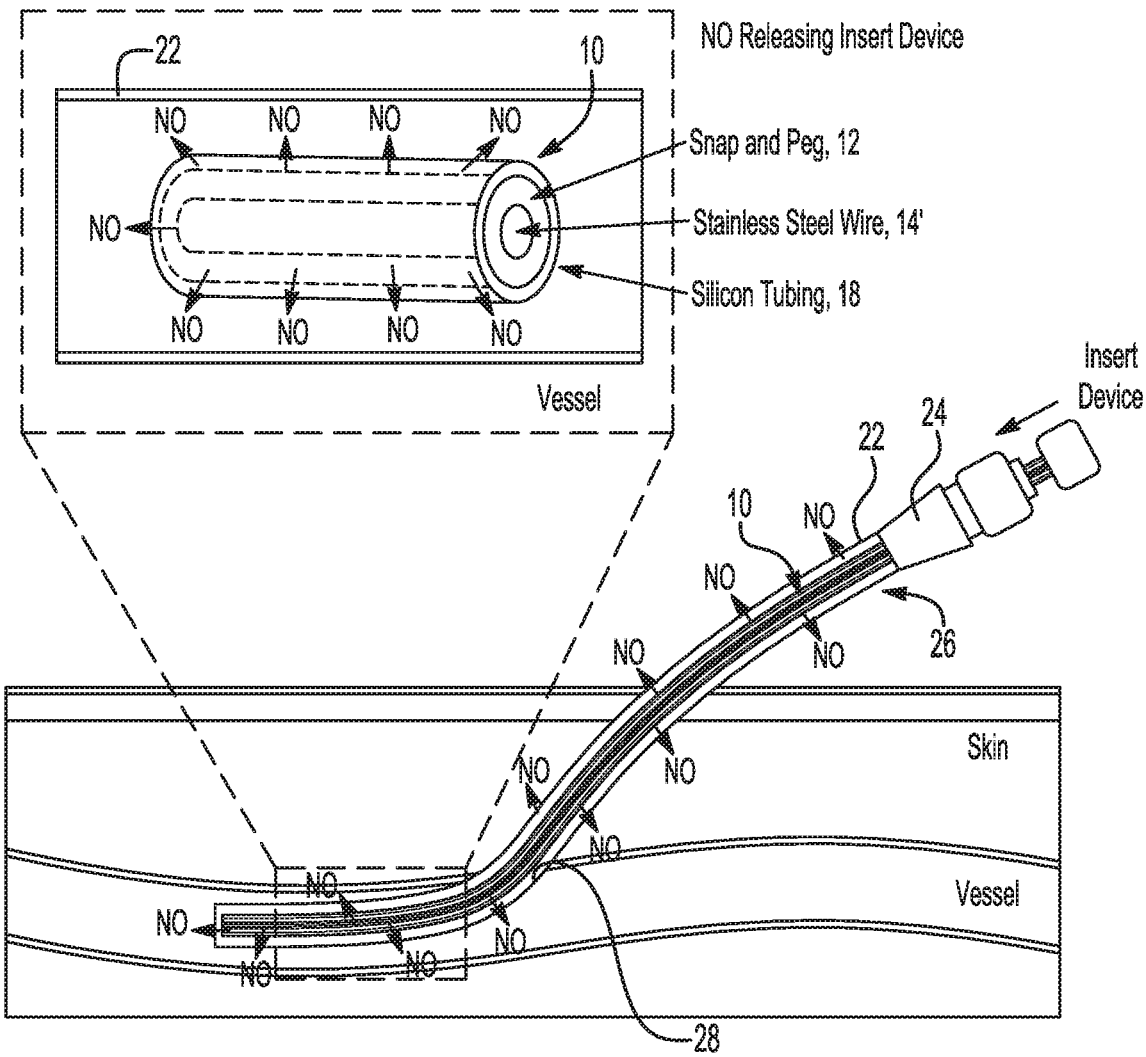
FIG. 2 is a schematic view of a catheter inserted into a patient and a catheter insert device inserted into the catheter, where the inset is a blown up view of the insert device inside of the catheter.
Figure 3:
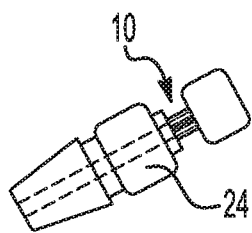
FIG. 3 is a schematic view of a catheter insert device inside of a hub adapter of a catheter.

The dimensions of the housing 16 may depend upon the catheter or the portion of the catheter (see reference numeral 26 in FIG. 2) in which the catheter insert device 10 is to be inserted. In some examples, the catheter insert device 10 may be configured to penetrate into the catheter tubing 22 past the patient's skin line and into the portion of the catheter tubing 22 that is within a blood vessel of the patient (e.g., as shown in FIG. 2). In these examples, the length of housing 16 is shorter than the length of the catheter 26, and the diameter of the housing 16 is smaller than the inner diameter of the catheter tubing 22. In some examples, the catheter insert device 10 penetrates several centimeters past the patient's skin line and into the portion of the catheter tubing 22 that is within a blood vessel of the patient. In other examples (e.g., as shown in FIG. 3), the catheter insert device 10 may be configured to penetrate into an adapter 24 (e.g., a hub) that is attached to a proximal end of the catheter tubing 22 and is in fluid communication with the catheter tubing 22. In these examples, the catheter insert device 10 does not penetrate past the patient's skin line or into the catheter tubing 22. Also in these examples, the length of housing 16 is shorter than the length of the adapter 24, and the diameter of the housing 16 is smaller than the inner diameter of the adapter 24. As examples, the outer diameter of the housing 16 (and thus of the catheter insert device 10) ranges from about 0.5 mm to about 3 mm, and the inner diameter of the housing 16 (and thus the diameter of the inner lumen 20) may range from about 0.1 mm to about 2.5 mm. When the housing 16 is to penetrate into the catheter tubing 22, the length may range from about 2 cm to about 20 cm, and when the housing 16 is to penetrate into the adapter 24, the length may range from about 1 cm to about 5 cm. In one example of the catheter insert device 10 suitable for use with the adapter 24, the length is about 2 cm.

In a method for making the catheter insert device 10, the powder composition 12 may be prepared and introduced into the housing 16. The housing 16 will then be sealed to prevent the powder composition 12 from leaching out of the housing 16.

The powder composition 12 may be introduced into the housing 16 as a powder formulation (e.g., the dry state), or in solution. As one example, the solid phase additive 14 may be mixed with the solid phase RSNO, and then the water uptake material may be added and the mixture may be further mixed. As another example, the solid phase additive 14 or the water uptake material may be mixed with the solid phase RSNO. Any of the dry powder examples may be loaded into the housing 16 using any suitable technique.

When the separate solid phase additive 14, such as the metal wire 14', is used, it may be inserted into the powder composition 12 that is present in the housing 16, or it may be introduced into the housing 16 before the powder composition 12 is added.

As another example, the powder composition 12 may be dissolved in a suitable solvent in order to create a homogeneous solution and to make it easier to fill the housing 16. The solvent may depend upon the components of the powder composition 12. In an example, tetrahydrofuran (THF) is a suitable solvent. Other suitable solvents may include ethanol and acetone. When a solvent is used, it is to be understood that the solvent is removed (e.g., allowed to fully evaporate) before sealing the housing 16. While the solvent may be desirable for achieving homogeneity and to simplify the filling process, a dry powder composition allows the RSNO to be more stable.

The housing 16 may then be sealed. Sealing may involve an adhesive or a mechanical sealing member (e.g., a cap, plug, etc.).

Any example of the catheter insert device 10 disclosed herein may be part of a kit. An example of the kit is shown in FIG. 2. In an example, the kit includes a catheter insert device 10, including: a powder composition 12 including a solid phase S-nitrosothiol (RSNO), an insert housing 16 including a polymeric wall 18 that is i) permeable to nitric oxide, ii) non-porous, and iii) permeable to water vapor, and an inner lumen 20 defined at least in part by the polymeric wall 18, wherein the powder composition 12 is completely sealed within the inner lumen 20 of the housing 16; and a catheter 26 including a catheter tubing 22 that is permeable to nitric oxide and has at least one lumen 28, and an adapter 24 attached to a proximal end of the catheter tubing 22 and having an opening that is operatively connected to the at least one lumen 28 of the catheter tubing 22; and a mechanism to lock the catheter insert device 10 in place within the at least one lumen 28 or within the adapter 24.

Any example of the powder composition 12 may be used in the kit.

The catheter 26 may be an acute catheter or a chronic catheter. In an example, the acute catheter is selected from the group consisting of an intravascular catheter and a urinary catheter; or the chronic catheter is selected from the group consisting of a tunneled dialysis catheter, a parenteral nutrition catheter, and a drug infusion catheter.

The catheter tubing 22 may be formed of any polymer material that is suitable for the application in which the polymer material is being used. A range of polymers may be used, including silicone rubber (SR), nylon (polyamide), polyurethane (PU), polyethylene terephthalate (PET), latex, and thermoplastic elastomers. When the walls of the catheter tubing 22 are permeable to nitric oxide (as shown in FIG. 2), the NO may also partition favorably out of the lumen 28 and the catheter tubing walls. Examples of NO permeable materials that may be used for the catheter tubing 22 include silicone rubber, polyurethane, copolymers of SR and PU, copolymers of PU and polycarbonate, and the other NO permeable materials. When the catheter tubing 22 is permeable to nitric oxide, the NO may be emitted over the entire outer surface of the catheter 26, which at least substantially prevents bacteria adhesion, biofilm formation, and clotting on the outer catheter surface. For example, the increased levels of NO that are generated will be therapeutic, and will be sufficient to help kill bacteria and viruses, disrupt bacterial biofilm formation, and disperse or prevent microbial biofilm formation (e.g., disperse antibiotic resistant biofilms). At the same time, even higher levels of NO will exist in the lock solution within the lumen 28 of the catheter 26, and this will prevent infection within that lumen and other lumens, if the catheter 26 is a multi-lumen catheter.

In one example, the adapter 24 is a Thouy-Borst adapter. In another example, the adapter 24 may be the hub region of a tunneled dialysis catheter (TDC). The adapter 24 may be permanently secured to the catheter tubing 22 or may be removable from the catheter tubing 22. The adapter 24 is wide enough to receive the catheter insert device 10, whether the device 10 extends into the adapter 24 but not into the catheter tubing 22, or whether the device 10 extends through the adapter 24 and into the catheter tubing 22. The adapter 24 may enable the insert device 10 be inserted into a lock solution present in the catheter 26, without initiating blood flow back up into the catheter 26.

The locking mechanism may be any suitable device that can lock the insert device 10 to the adapter 24. The locking mechanism may be attached at one end of the insert device 10. As one example, the locking mechanism may be a screw-like cap located at a proximal end of the insert device 10 and may attach to a proximal end of the adapter 24. As one example, the locking mechanism may include a cap with male threads that interlock with female threads defined the proximal end of the adapter 24. Other examples of the locking mechanism include a clip like mechanism. This mechanism can be pushed so that the clip puts pressure on the walls of the catheter and seals the inner lumen. This prevents material from going in or coming out. The clip can also put pressure on the insert device 10 to lock it in place.

A method for using the catheter insert device 10 includes locking the catheter insert device 10 into place within a lumen 28 of a catheter 26 or within an adapter 24 operatively connected to the catheter 26, whereby the catheter insert device 10 is placed into contact with a lock solution in the lumen 28 or within the adapter 24. Any example of the catheter insert device 10 may be used in the method. The catheter insert device 10 may be inserted into an opening in the adapter 24, as illustrated in FIG. 2. The catheter insert device 10 may then be slid into place and locked via the locking mechanism.

Prior to inserting the catheter insert device 10, the method may further include introducing the catheter lock solution into the lumen 28 of the catheter 26. A syringe (or other suitable instrument) may be used to take up the catheter lock solution (from a container) and to introduce the catheter lock solution into the lumen 28.

In the dry state, the RSNO in the powder composition 12 is relatively stable (e.g., for at least 3 months). Once the catheter insert device 10 is in contact with the catheter lock solution, water vapor will permeate through the polymeric wall(s) 18 of the housing 16 and initiate decomposition of the S-nitrosothiol, which generates the nitric oxide. The nitric oxide permeates through the polymeric wall(s) 18 into the lumen 28 of the catheter 26. When the wall(s) of the catheter 26 are permeable to nitric oxide, the NO may also permeate through to the exterior of the catheter 26. The presence of the solid phase additive 14, 14' can accelerate the rate of release of nitric oxide from the RSNO after exposure to water vapor, and the presence of the water uptake material can increase the amount of water vapor and/or the rate at which water vapor is taken into the insert catheter device 10.

The device 10 can begin to release NO relatively quickly, e.g., within 5 minutes, and then can continuously release NO at relatively high levels for an extended time period (e.g., at least 24 hours, or at least 48 hours, or at least 72 hours).

The amount of NO that is generated can be precisely controlled by varying the weight percentage of the S-nitrosothiol, the weight percentage solid phase accelerant/additive 14, the thickness of the insert walls 18, the permeability of the insert walls 18, etc.

The catheter insert device 10 may remain in the catheter 26 for a predetermined time, depending upon the type of catheter 26. For example, the catheter insert device 10 may remain in the catheter 26 for any time ranging from 1 hour to about 3 days (72 hours). In one example it may be desirable to utilize the catheter insert device 10 in a tunneled dialysis catheter after each dialysis session. In this example, NO release for about 2 to 3 days would be desirable.

To further illustrate the present disclosure, examples are given herein. It is to be understood that these examples are provided for illustrative purposes and are not to be construed as limiting the scope of the present disclosure.

EXAMPLES

Example 1

NO-Releasing Insert Device

Example catheter insert devices were prepared. The powder composition included 80 wt % SNAP (as the solid phase S-nitrosothiol) and 20 wt % PEG (MW=4,000 g/mol) (as the water uptake material). The powder composition was dissolved in THF to obtain a homogeneous solution. The solution was added to 0.94 mm outer diameter/0.51 mm inner diameter silicone rubber tubing. 0.3 mm stainless steel wires (316L) (as the solid phase additive) were also added to each tubing piece. The THF was evaporated off by allowing the filled tubing to remain sitting at room temperature, under a hood for at least 24 hours to allow full evaporation so that the inner components were dry and in solid form. The tubings were then sealed with DOWSIL™ 3140 RTV clear silicone coating MIL-A-46146 and allowed to cure/fully seal.

NO Release Profile Tests

Figure 4A:
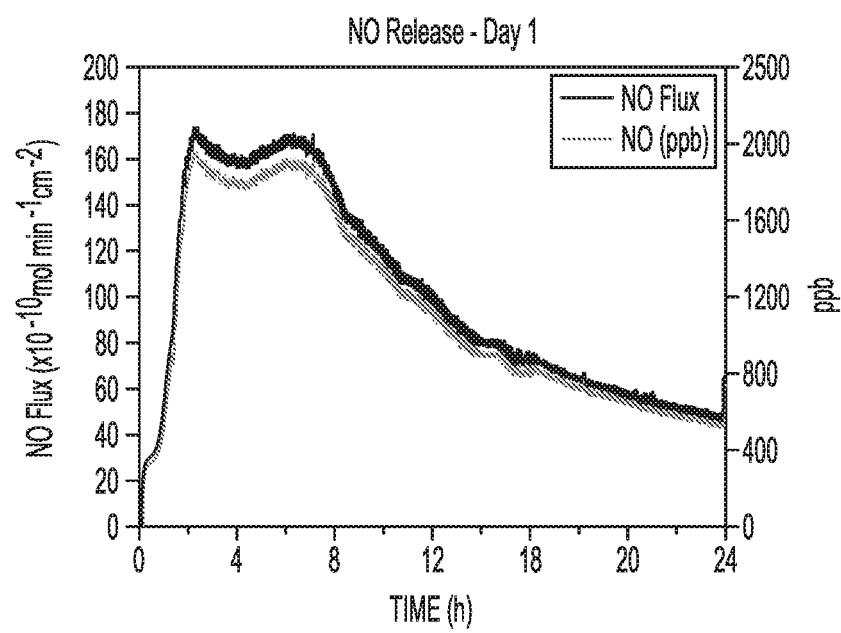
FIGS. 4A through 4D are graphs depicting, on the left Y axis, nitric oxide (NO) release profiles (in terms of NO surface flux ($\times 10^{-10}$ mol min$^{-1}$cm$^{-2}$) versus time (hours, h)), and, on the right Y axis, the modulation of nitric oxide generation (in terms of the NO ppb level versus time (hours)) for an example of the catheter insert device including 80 wt % S-nitroso-N-acetyl-penicillamine (SNAP), 20 wt % poly(ethylene glycol), and a stainless steel wire on day 1 (FIGS. 4A and 4B), day 2 (FIG. 4C), and day 4 (FIG. 4D) of being inserted into a catheter filled with phosphate-buffered saline (PBS)
Figure 4B:
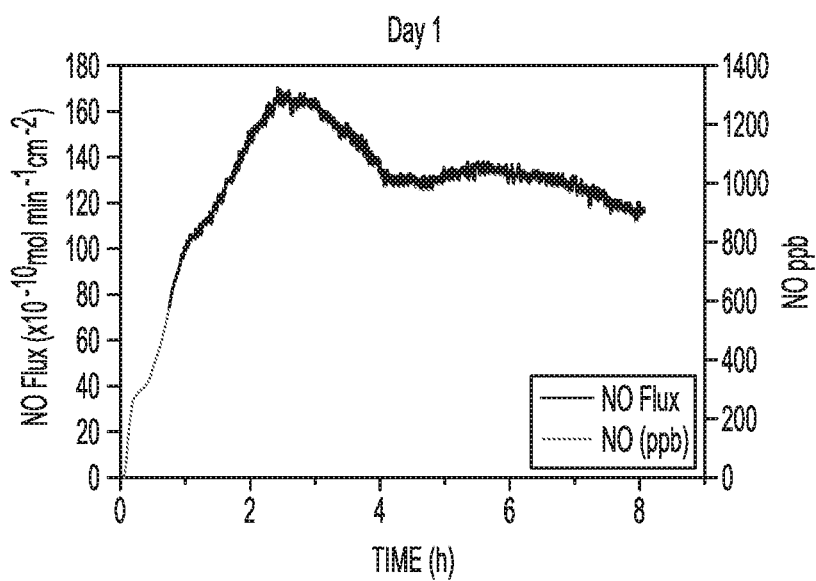
Figure 4C:
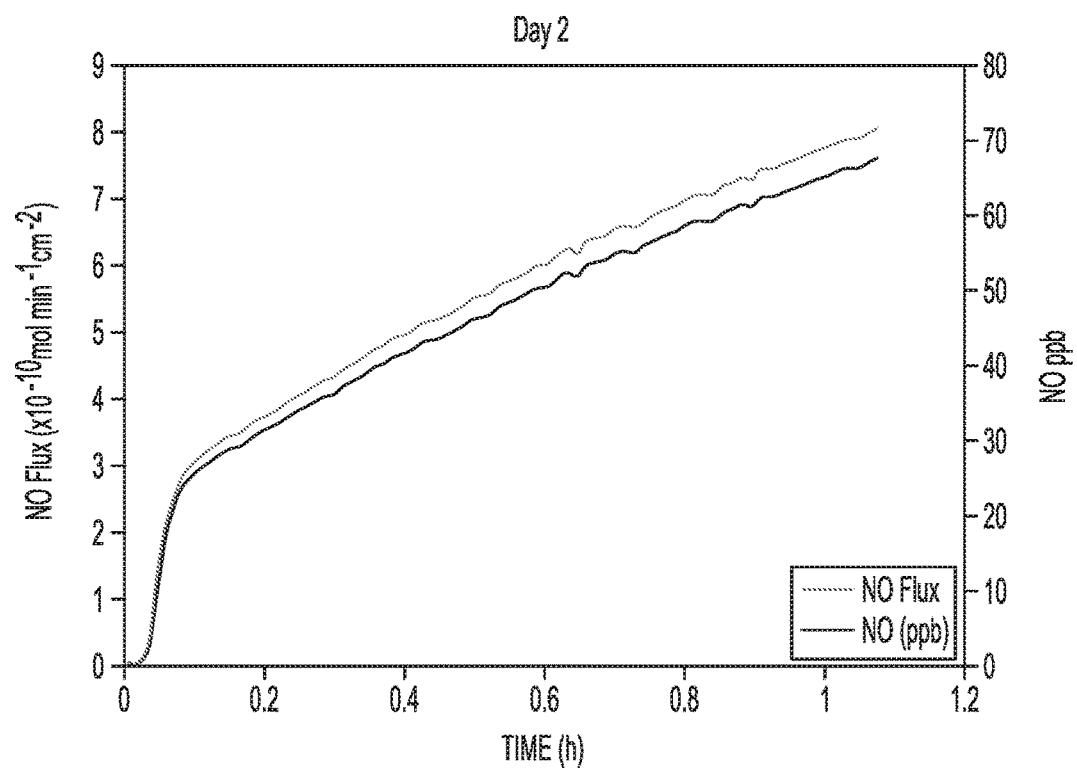
Figure 4D:
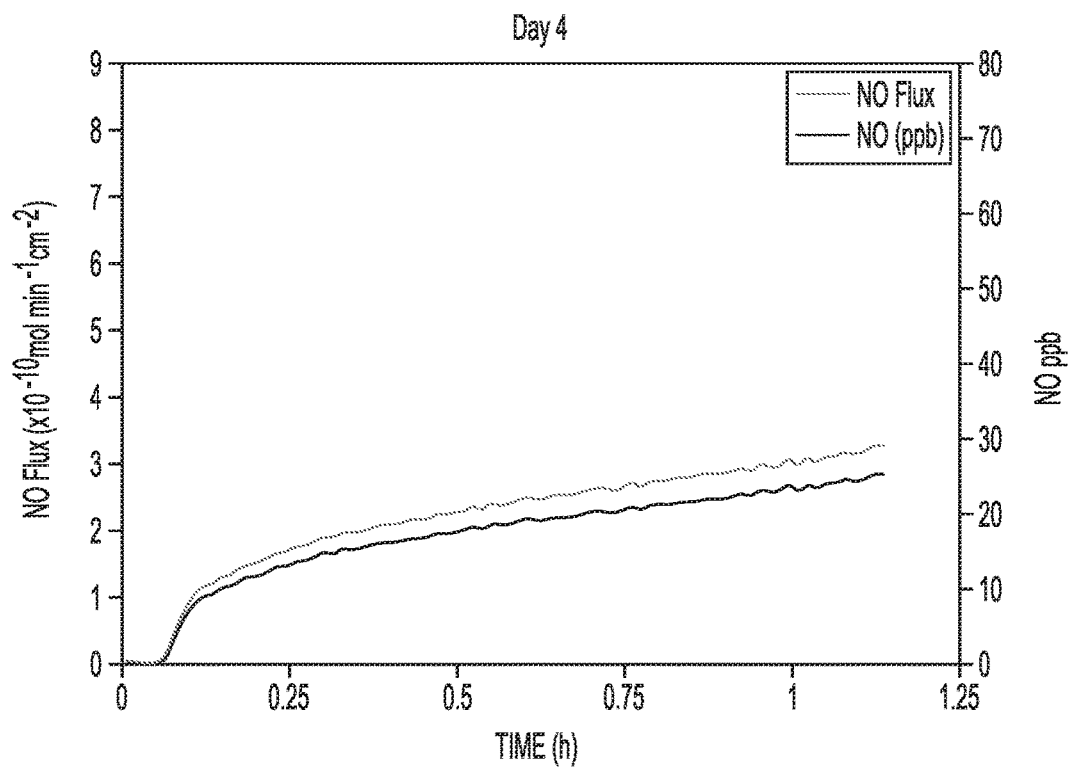

One example catheter insert device was soaked in phosphate-buffered saline for four days, and the released nitric oxide was detected by a chemiluminescence-based nitric oxide analyzer. The NO release profiles (left Y axis) for the first 8 hours are shown in FIG. 4B, for the first day (24 hours) are shown in FIG. 4A, for 1.25 hours of the second day are shown in FIG. 4C, and for 1.25 hours of the fourth day are shown in FIG. 4C. These graphs also depict the NO levels (ppb) (right Y axis). Day 1 had high NO release due to a SNAP "NO-burst" effect, which occurs when SNAP is initially hydrated. Thus effect was further catalyzed by the stainless steel. The results for Day 2 and Day 4 indicate that NO release gradually increases over time.

Stability Tests

Figure 5A:
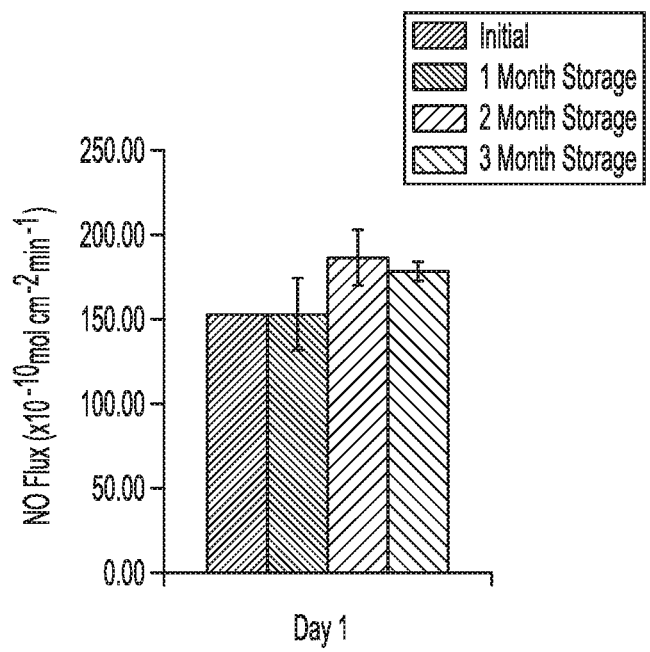
FIGS. 5A through 5C are graphs depicting nitric oxide (NO) release profiles (in terms of NO flux ($\times 10^{-10}$ mol min$^{-1}$cm$^{-2}$) at a particular day of a storage period) for example catheter insert devices stored at 23° C. for an initial storage period, a 1 month storage period, a 2 month storage period, and a 3 month storage period, where each sample was measured on day 1 of the storage period (FIG. 5A), day 2 of the storage period (FIG. 5B), and day 4 of the storage (FIG. 5C)
Figure 5B:
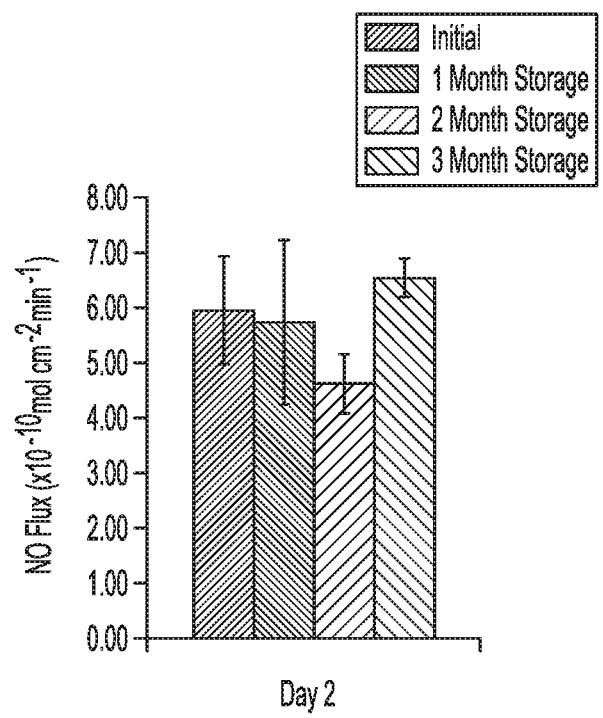
Figure 5C:
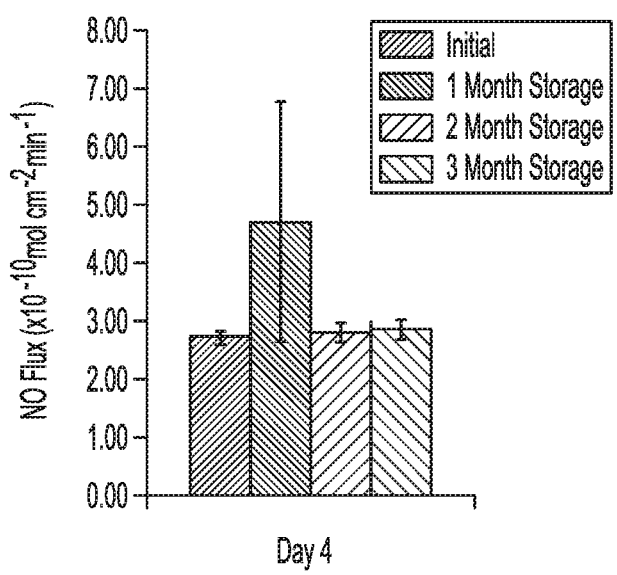

At three different stability time periods, three insert devices were tested for stability at 23° C. The stability time periods included after 1 month of storage, after 2 months of storage, and after 3 months of storage. Stability measurements were taken on days 1, 2, and 4 of each stability time period. Initial stability measurements (referred to as "Initial" in FIG. 5A through FIG. 5C) were also taken the day the device was prepared (Day 1), the day after the device was prepared (Day 2), and 3 days after the device was prepared (Day 4). The stability measurements were taken with a chemiluminescence-based nitric oxide analyzer. The results taken on Day 1 of the initial time period and each of the stability time periods are shown in FIG. 5A; the results taken on Day 2 of the initial time period and each of the stability time periods are shown in FIG. 5B; and the results taken on Day 4 of the initial time period and each of the stability time periods are shown in FIG. 5C. It is noted that for the initial Day 1 measurement, only two devices were tested. In FIG. 5A on the Day 1, the inserts released very high amounts of NO due to SNAP initial exposure to water. The initial hydration of SNAP lead to an NO-burst effect. Additionally, because the wall of the silicone tubing was very thin, the initial exposure to water lead to hydration of SNAP crystals closest to the outer diameter/circumference of the silicone. This resulted in a high burst and release of NO. Then, as water continued to be absorbed towards the center of the insert, more SNAP was hydrated over time and NO released. The results illustrate that the inserts are stable for at least 3 months.

Example 2

NO-Releasing Insert Devices and Control Insert Devices

Example insert devices as described in Example 1 were prepared.

Control catheter insert devices were also prepared. The powder composition included 100 wt % PEG and a stainless steel wire (no SNAP was included). The powder composition was dissolved in THF to obtain a homogeneous solution. The solution was added to 0.94 mm outer diameter/0.51 mm inner diameter silicone rubber tubings. 0.3 mm stainless steel wires (316L) were also added to each tubing. The THF was evaporated off by allowing the filled tubing to remain sitting at room temperature, under a hood for at least 24 hours to allow full evaporation so that the inner components were dry and in solid form. The tubings were then sealed with DOWSIL™ 3140 RTV clear silicone coating MIL-A-46146 and allowed to cure/fully seal.

Biofilm Tests

A CDC Biofilm reactor was used, including 10% LB (lysogeny broth) medium. Polyurethane (PU) catheters having a 1.96 mm outer diameter, a 1.14 mm inner diameter, and a wall thickness of 0.41 mm were used. In the CDC Biofilm reactor, the PU catheter tubing was sealed at one end with an epoxy sealant and was open to the medium at the other end.

A three-day biofilm test was performed. The open end of the PU catheter was exposed to either *P. Aeruginosa* or *S. Aureus*. Every 24 hours, the example insert device or the control insert device was inserted into the PU catheter. The complete bacterial count on the outer (exterior) surface of the PU catheters was determined.

Figure 6A:
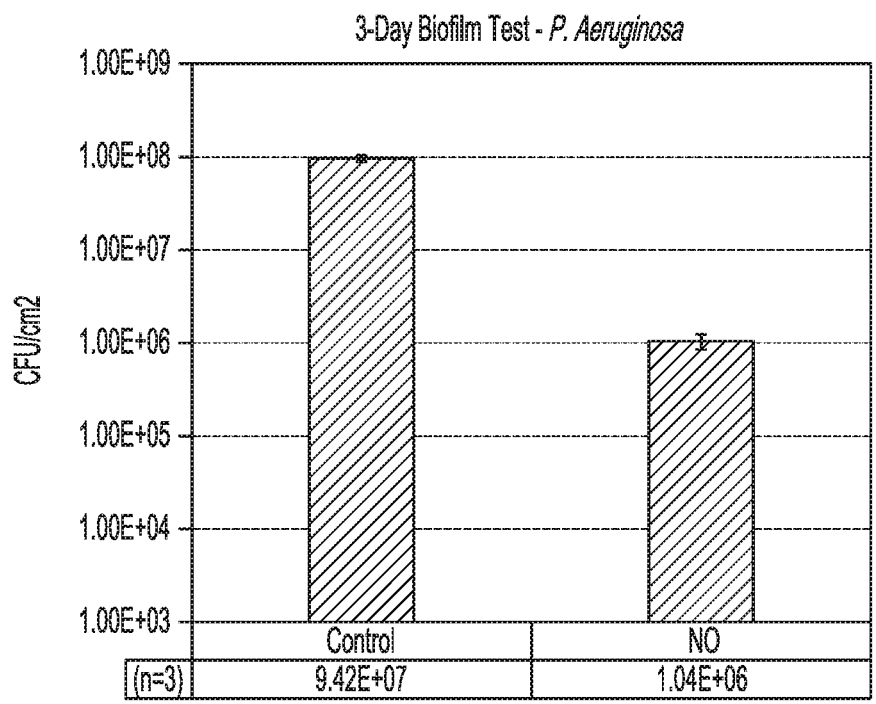
FIGS. 6A and 6B are graphs depicting the antimicrobial activity (colony-forming unit (CFU)/cm$^2$) toward *P. Aeruginosa* and *S. Aureus* on the exterior surface of polyurethane catheters treated with a SNAP-PEG (80/20 wt %) stainless steel-containing catheter insert devices (n=3 test catheters) and on the exterior surface of polyurethane catheters treated with PEG (100 wt %, inert, no SNAP) stainless steel-containing insert devices (n=3 control catheters) in a CDC bioreactor over a 3-day biofilm test.
Figure 6B:
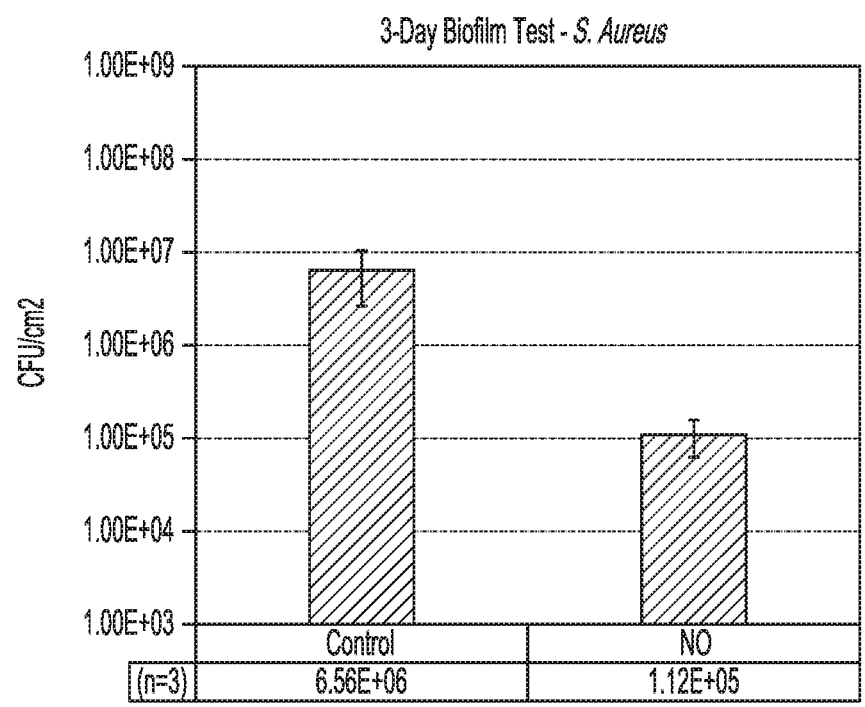

The antimicrobial activity toward *P. Aeruginosa* of the example insert devices (n=3) in PU catheters and of the control insert device (n=3) in PU catheters over the 3-day biofilm test are shown in FIG. 6A. The antimicrobial activity toward *S. Aureus* of the example insert devices (n=3) in PU catheters and of the control insert device (n=3) in PU catheters over the 3-day biofilm test are shown in FIG. 6B. These results clearly indicate that the NO-releasing example insert devices reduce biofilm formation.

Figure 7A:
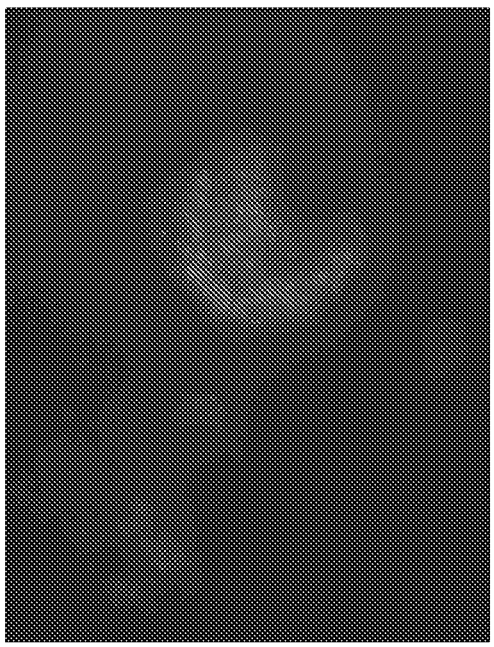
FIGS. 7A and 7B are black and white reproductions of originally colored confocal images depicting the results of the 3-day biofilm test of *P. Aeruginosa* for one of the control catheters (FIG. 7A) and for one of the test catheters (FIG. 7B), where green staining depicted live bacteria and red (not readily visible) depicted dead bacteria.
Figure 7B:
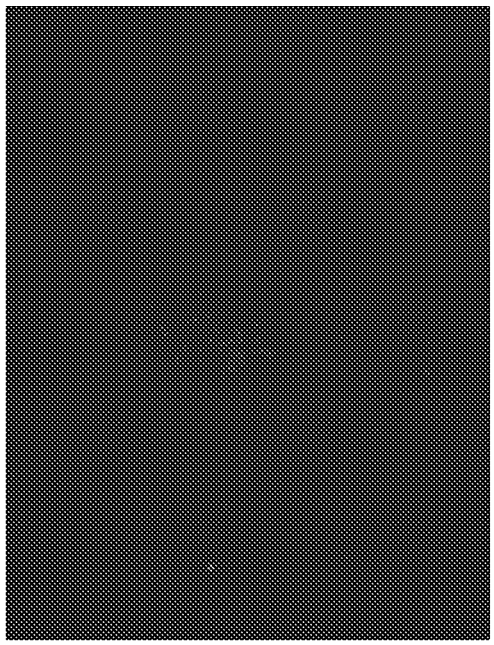

Black and white reproductions of the originally colored confocal images for 3-day biofilm test of P. Aeruginosa are shown in FIGS. 7A and 7B for one of the control insert devices and one of the example insert devices, respectively. There were more live bacteria on the PU catheter with the control insert device (FIG. 7A) than on the on the PU catheter with the example insert device (FIG. 7B).

Figure 8A:
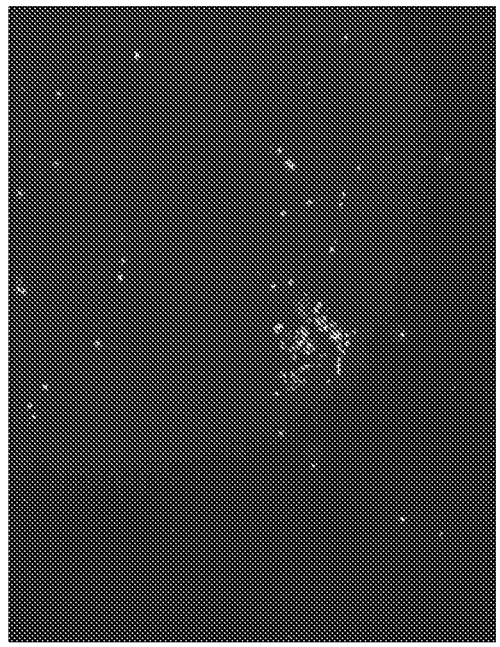
FIGS. 8A and 8B are black and white reproductions of originally colored confocal images depicting the results of the 3-day biofilm test of *S. Aureus* for one of the control catheters (FIG. 8A) and for one of the test catheters (FIG. 8B), where green staining depicted live bacteria and red (not readily visible) depicted dead bacteria.
Figure 8B:
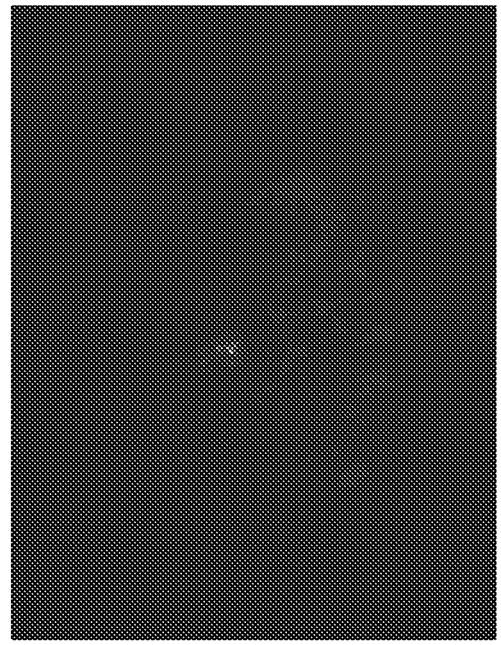

Black and white reproductions of the originally colored confocal images for 3-day biofilm test of S. Aureus are shown in FIGS. 8A and 8B for one of the control insert devices and one of the example insert devices, respectively. There were more live bacteria on the PU catheter with the control insert device (FIG. 8A) than on the on the PU catheter with the example insert device (FIG. 8B).

A five-day biofilm test was performed with S. Aureus. The open end of the PU catheter was exposed to S. Aureus. Every 24 hours, the example insert device or the control insert device was inserted into the PU catheter. The complete bacterial count on the outer (exterior) surface of the PU catheters was determined.

Figure 9:
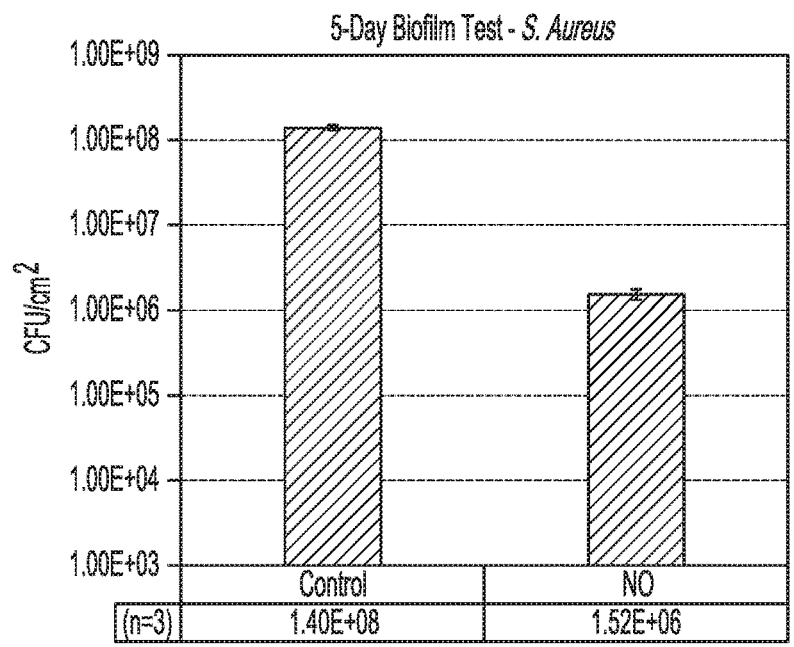
FIG. 9 is a graph depicting the antimicrobial activity (CFU/cm$^2$) toward *S. Aureus* on the exterior surface of polyurethane catheters treated with SNAP-PEG (80/20 wt %) stainless steel-containing catheter insert devices (n=3 test catheters) and on the exterior surface of polyurethane catheters treated with PEG (100 wt %, inert, no SNAP) stainless steel-containing insert devices (n=3 control catheters) in a CDC bioreactor over a 5-day biofilm test.

The antimicrobial activity toward S. Aureus of the example insert devices (n=3) in PU catheters and of the control insert device (n=3) in PU catheters over the 5-day biofilm test are shown in FIG. 9. These results clearly indicate that the NO-releasing example insert devices reduce biofilm formation when compared to the control insert devices.

Figure 10A:
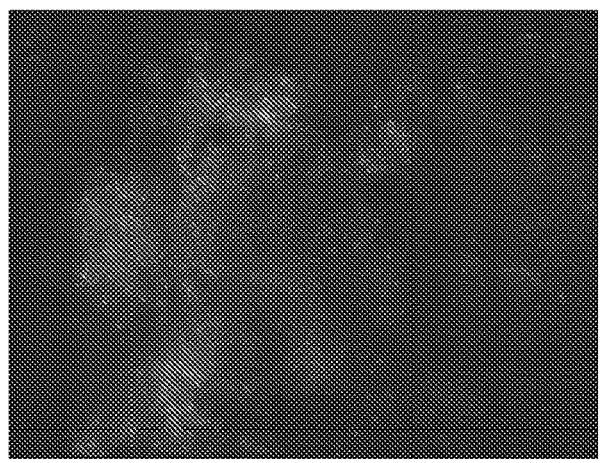
FIGS. 10A and 10B are black and white reproductions of originally colored confocal images depicting the results of the 5-day biofilm test of *S. Aureus* for one of the control catheters (FIG. 10A) and for one of the test catheters (FIG. 10B), where green staining depicted live bacteria and red (not readily visible) depicted dead bacteria.
Figure 10B:
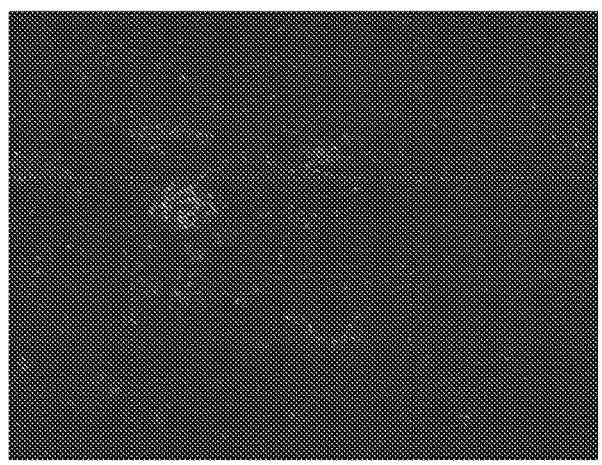

Black and white reproductions of the originally colored confocal images for 5-day biofilm test of S. Aureus are shown in FIGS. 10A and 10B for one of the control insert devices and one of the example insert devices, respectively. There were more live bacteria on the PU catheter with the control insert device (FIG. 10A) than on the on the PU catheter with the example insert device (FIG. 10B).

Dispersal Tests

A CDC Biofilm reactor was used, including 10% LB medium. Polyurethane (PU) catheters having a 1.96 mm outer diameter, a 1.14 mm inner diameter, and a wall thickness of 0.41 mm were used. In the CDC Biofilm reactor, the PU catheter tubing was sealed at one end with an epoxy sealant and was open to the medium at the other end. Either P. Aeruginosa or S. Aureus was allowed to grow on the outer surface of the PU catheter tubing over a 3-day period. Then, the example insert device or the control insert device was placed in the PU catheter tubing on the $4^{th}$ day and remained therein for 1 day (24 hours). The complete bacterial count on the outer surface of the PU catheters was determined on the $5^{th}$ day.

Figure 11A:
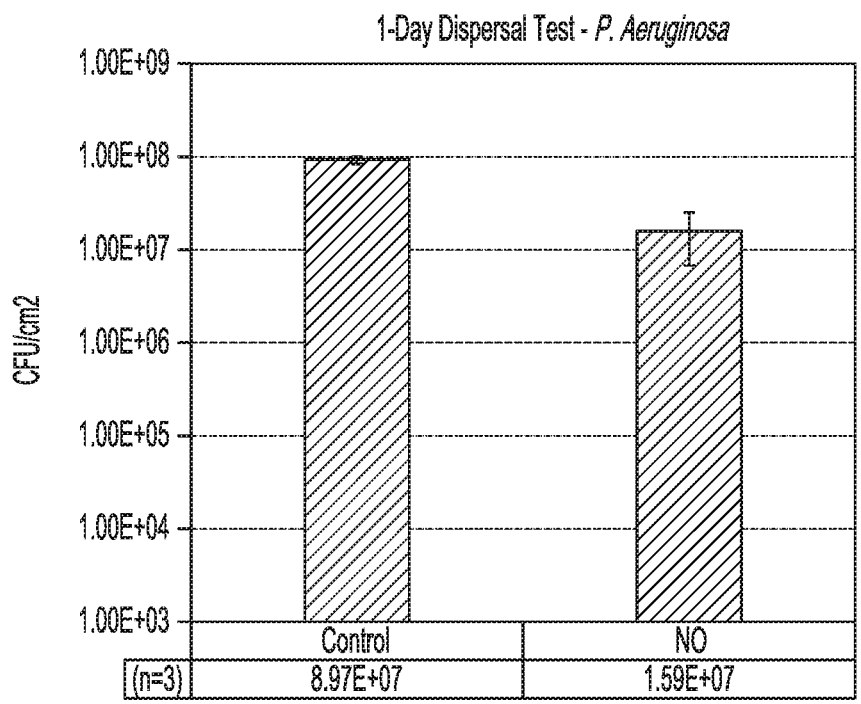
FIGS. 11A and 11B are graphs depicting the antimicrobial activity (CFU/cm$^2$) toward *P. Aeruginosa* and *S. Aureus* on the exterior surface of polyurethane catheters treated with SNAP-PEG (80/20 wt %) stainless steel-containing catheter insert devices (n=3 test catheters) and PEG (100 wt %, inert, no SNAP) stainless steel-containing insert devices (n=3 control catheters) in a CDC bioreactor over a 4-day dispersal test (in which biofilm were grown on the exterior surfaces for 3 days, then the polyurethane catheters treated with SNAP-containing or control (no SNAP-containing) insert devices for 1 day)
Figure 11B:
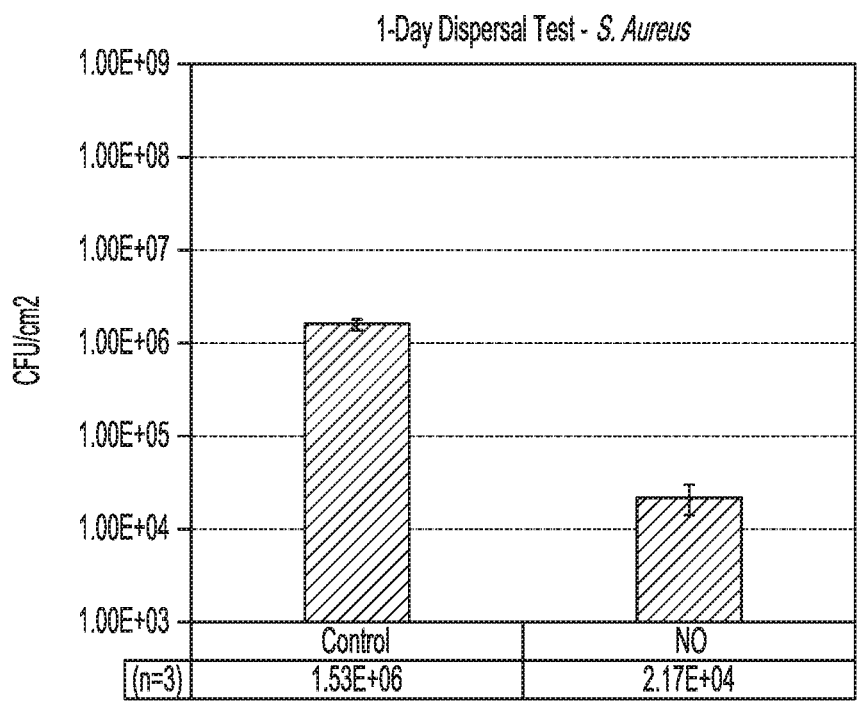

The antimicrobial activity toward P. Aeruginosa of the example insert devices (n=3) in PU catheters and of the control insert device (n=3) in PU catheters over the 3-day dispersal test are shown in FIG. 11A. The antimicrobial activity toward S. Aureus of the example insert devices (n=3) in PU catheters and of the control insert device (n=3) in PU catheters over the 3-day dispersal test are shown in FIG. 11B. These results clearly indicate that the NO-releasing example insert devices disperse biofilms better than the control insert devices.

Figure 12A:
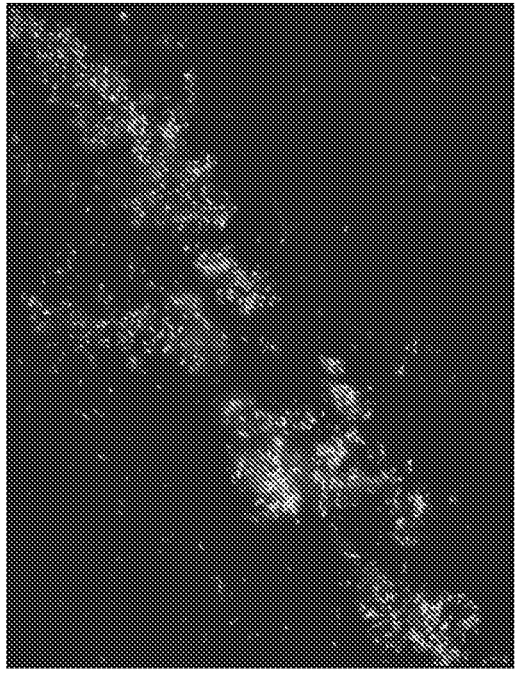
FIGS. 12A and 12B are black and white reproductions of originally colored confocal images depicting the results of the 4-day dispersal test of *P. Aeruginosa* for one of the control catheters (FIG. 12A) and for one of the test catheters (FIG. 12B), where green staining depicted live bacteria and red (not readily visible) depicted dead bacteria.
Figure 12B:
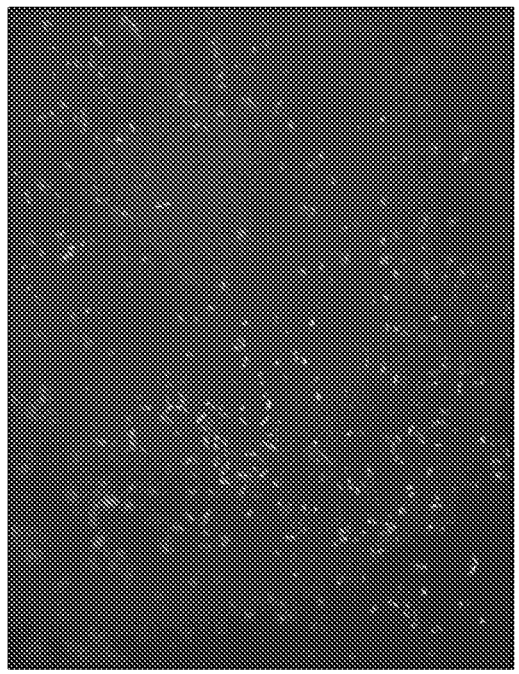

Black and white reproductions of the originally colored confocal images for 3-day dispersal test of P. Aeruginosa are shown in FIGS. 12A and 12B for one of the control insert devices and one of the example insert devices, respectively. There were more live bacteria on the PU catheter with the control insert device (FIG. 12A) than on the on the PU catheter with the example insert device (FIG. 12B).

Figure 13A:
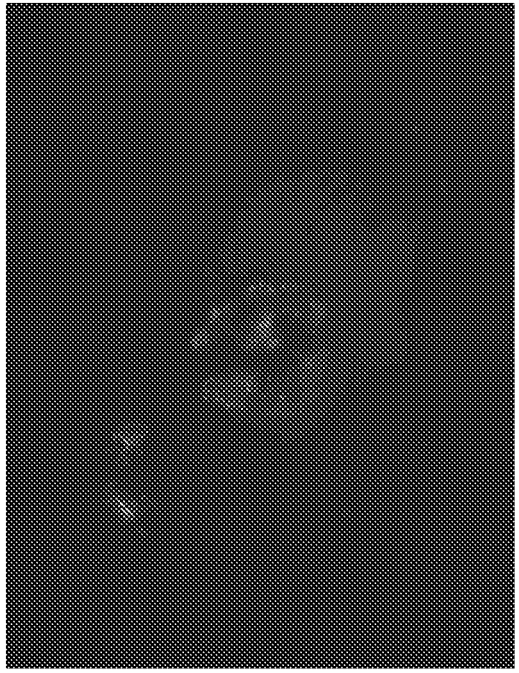
FIGS. 13A and 13B are black and white reproductions of originally colored confocal images depicting the results of the 4-day dispersal test of *S. Aureus* for one of the control catheters (FIG. 13A) and for one of the test catheters (FIG. 13B), where green staining depicted live bacteria and red (not readily visible) depicted dead bacteria.
Figure 13B:
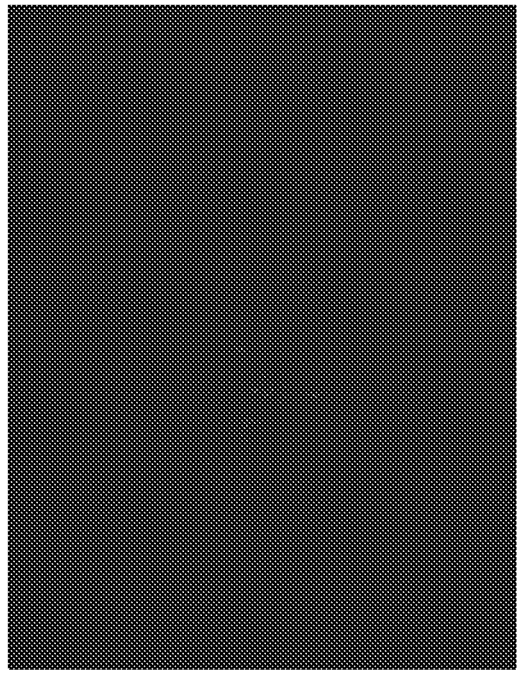

Black and white reproductions of the originally colored confocal images for 3-day dispersal test of S. Aureus are shown in FIGS. 13A and 13B for one of the control insert devices and one of the example insert devices, respectively. There were more live bacteria on the PU catheter with the control insert device (FIG. 13A) than on the on the PU catheter with the example insert device (FIG. 13B).

Inner Lumen Antimicrobial Test

In this 5-day test, a flow cell system was used. The inner lumen of PU catheters was inoculated with bacteria (P. Aeruginosa or S. Aureus). Fresh media flow occurred 3 times a day for 1 hour, and for the remainder of the day, flow was stopped. The NO-releasing example insert devices or the control insert devices were placed inside the inner lumens. Media remained in the inner lumen when the inserts were placed therein, in part because it was difficult to flush out without contamination. One end of the catheter was open to air; and the other end was connected to a pipette tip of media flow connector system. Fresh inserts were used for each day.

Figure 14A:
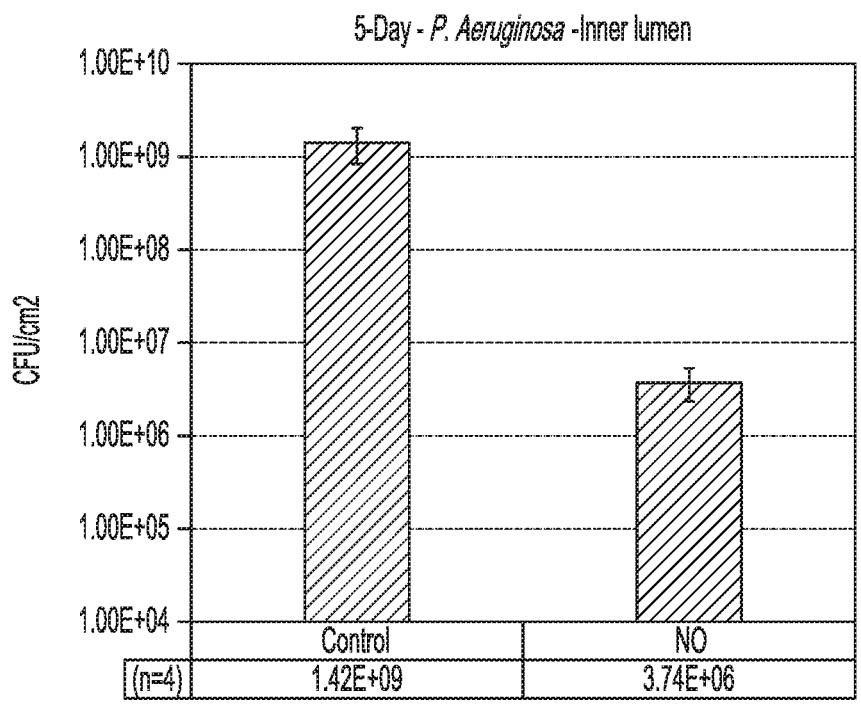
FIGS. 14A and 14B are graphs depicting the antimicrobial activity (CFU/cm$^2$) toward *P. Aeruginosa* and *S. Aureus* on the interior surface of polyurethane catheters treated with SNAP-PEG (80/20 wt %) stainless steel-containing catheter insert devices (n=3 test catheters) and PEG (100 wt %, inert, no SNAP) stainless steel-containing insert devices (n=3 control catheters) in a flow cell system over a 5-day biofilm test.
Figure 14B:
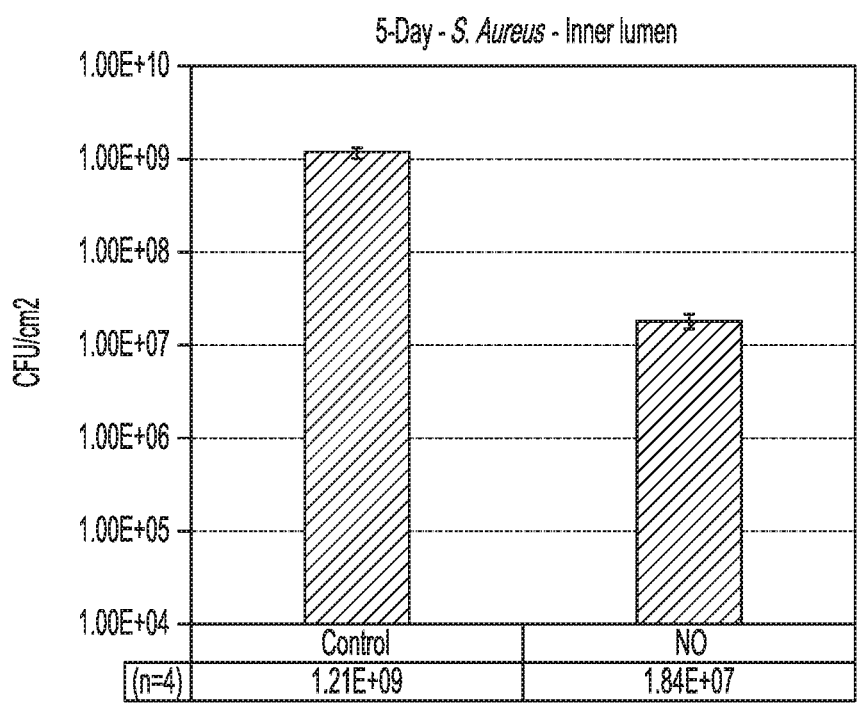

The antimicrobial activity toward P. Aeruginosa of the example insert devices (n=4) in PU catheters and of the control insert device (n=4) in PU catheters over the 5-day inner lumen biofilm test are shown in FIG. 14A. The antimicrobial activity toward S. Aureus of the example insert devices (n=4) in PU catheters and of the control insert device (n=4) in PU catheters over the 5-day inner lumen biofilm test are shown in FIG. 14B. These results clearly indicate that the NO-releasing example insert devices reduce biofilm formation when compared to the control insert devices.

All of the results of Example 2 indicate that the presence of the stainless steel wire as the solid phase additive significantly enhances the effect of the nitric oxide.

Example 3

NO-Releasing Insert Devices and Control Insert Devices

The dimensions of the NO releasing inserts were designed based on the hub dimensions of commonly used hemodialysis catheters.

All of the catheter insert devices were prepared in the absence of direct light.

A silicone tubing (inner diameter (ID) 0.058", outer diameter (OD) 0.077") was cut into about 3 cm segments, each of which was sealed at one end using an adhesive glue (DOWSIL™ 3140 RTV clear silicone coating MIL-A-46146), which was allowed to dry for about 24 hours. Then, 12±0.2 mg of a desired dry powder formulation was dispensed into a respective tubing segment using a glass funnel pipet. The dry powder formulations used included (example A) 75 wt % GSNO: 25 wt % 30 nm size ZnO nanoparticles; (example B) 25 wt % GSNO: 75 wt % 30 nm size ZnO nanoparticles; (example C) 60 wt % GSNO: 20 wt % 30 nm size ZnO nanoparticles: 20 wt % solid polyethylene glycol (MW=3,350) (PEG); (comp. example D) 75 wt % GSNO: 25 wt % fumed silica. Before use, the GSNO was crushed into a fine powder using a mortar and pestle and mixed with the other component(s) by vortexing for about 1 minute to achieve a homogeneous dry powder mixture. After filling the tubing with the desired powdered formulation (about 12 mg 1.8 cm fill length), the end that was used to fill the tubing segment was cut to obtain about 0.2 cm of head space above the fill powder. The adhesive glue was used to seal the open end and was allowed to dry for about 24 hours. The final length of each insert was about 2.0 cm.

NO Release Profile Tests

Nitric oxide release from the NO releasing inserts (examples A-C, comp. example D) was measured using a chemiluminescence-based nitric oxide analyzer (NOA). The NOA was first calibrated via a two-point calibration of $N_2$ gas passed through an NOA zero air filter and a standard of 44.3 ppm NO in $N_2$ gas.

A saline solution (0.9% sodium chloride) was made using 18.2 M S2 deionized water. The NOA sample cell was filled with 11 mL of saline solution and the NO releasing insert was placed below a floating polypropylene barrier to keep the insert fully submerged at all times. The saline solution reservoir was bubbled with $N_2$ gas at a rate of 50 mL/min to allow the NO generated from GSNO to escape from the solution and be carried into the NOA by the $N_2$ sweep gas. All NOA sample cells were wrapped in aluminum foil to shield the samples from light exposure. The NO release was continuously monitored for 72 hours at room temperature (24° C.).

The conditions for this test were selected to mimic real world conditions of hemodialysis catheter hubs. Measuring over a 72 hour period was chosen because hemodialysis treatments normally occur every 2 to 3 days, enabling the NO release insert to be changed at each dialysis session. The other conditions were chosen because catheter hubs are located outside of the body, opaque, and locked with a saline lock solution.

Figure 15:
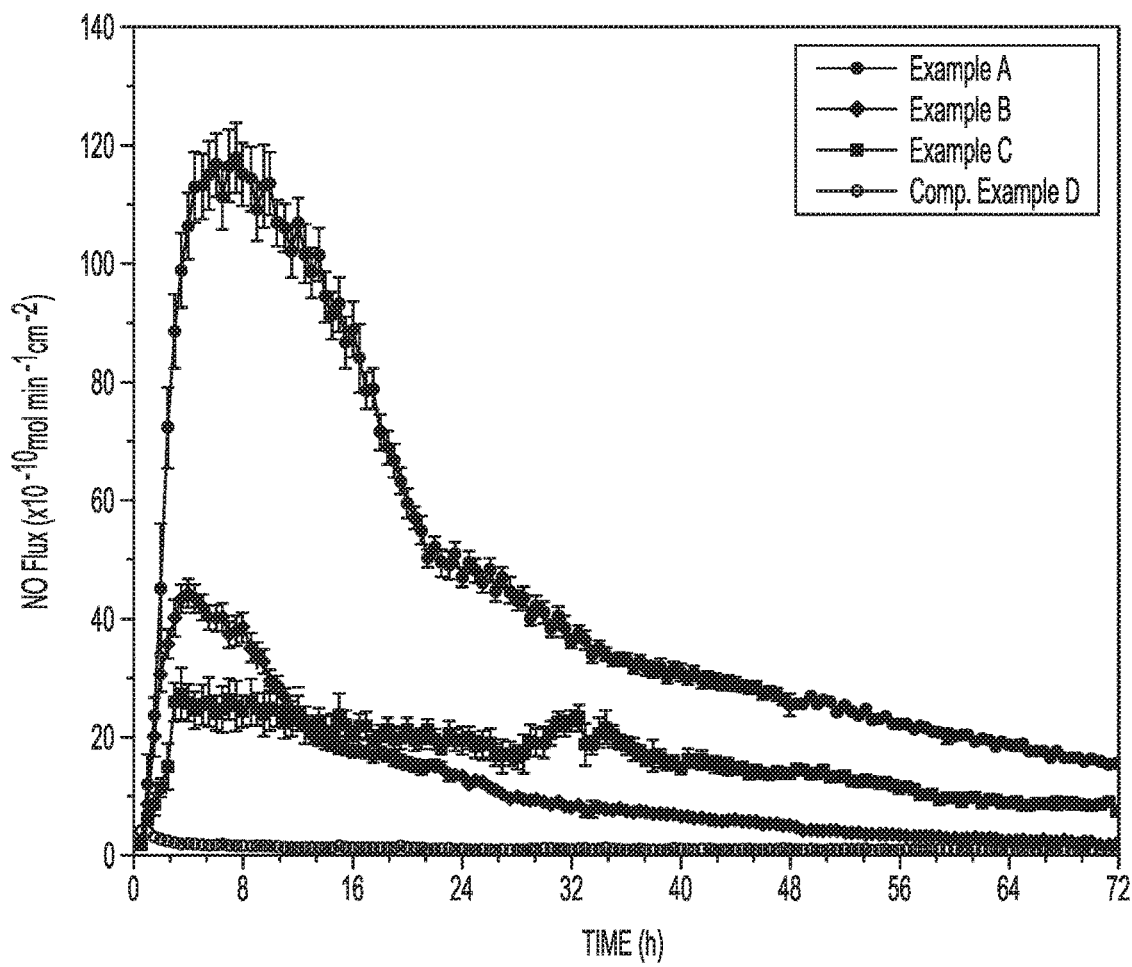
FIG. 15 is a graph depicting nitric oxide (NO) release profiles (in terms of NO surface flux (x10$^{-1}$mol min$^{-1}$cm$^{-2}$) versus time (in hours) for three example catheter insert devices (including S-nitrosoglutathione (GSNO) and 30 μm zinc oxide particles or 30 μm zinc oxide particles and polyethyleneglycol (PEG)) and a control insert device including 75 wt % S-nitrosoglutathione (GSNO) and 25 wt % inert fumed silica particles (data represents mean ±standard deviation, n=3)

The results are shown in FIG. 15. Example A yielded a large burst of NO over the first 24 hours and tapered off until the 72 hour mark was reached. For example B, the percentages of GSNO and ZnO were reversed compared to example A. Example B demonstrated a similar NO release profile compared to example A, however the initial burst lasted only 12 hours and tapered off significantly afterwards due to the lower amount of GSNO initially present. The results for example B illustrate that more of the RSNO is needed for long term release.

In attempt to level/smooth out the NO release profile of example A example C was prepared with polyethylene glycol (MW=3,350) (PEG). The PEG was added to increase the viscosity of the insert's internal components (GSNO and ZnO). As shown in FIG. 15, the leveling/smoothing effect was achieved, which lead to a more consistent NO release rate over 72 hour period.

To prove that ZnO enhanced NO release in each of examples A, B and C, fumed silica particles were substituted in place of ZnO in comp. example D. The fused silica particles were an inert agent that does not react with GSNO. The NO release profile of comp. example D shows minimal NO release over 72 hours. This data illustrates that ZnO enhances NO release from GSNO contained within silicone rubber tubing.

In Vitro Simulated Catheter Hub Tests

Examples A, B, and C displayed unique NO releasing profiles over 72 hours. Therefore, each was tested for their bactericidal effects using a simulated hub antimicrobial experiment. This experiment was designed to mimic the conditions of a real hemodialysis catheter hub.

To simulate the hub region of a catheter, 3 cm of silicone tubing (ID 0.125", OD 0.250") was employed. A volume of 0.3 mL of overnight grown bacteria cultures (1×108 CFU/mL) in 10% LB broth was transferred into the simulated hub clamped at one end. Then, a NO releasing insert was placed inside of the simulated hub and the other end was clamped shut. For control samples, no NO releasing insert was added. Each sample was incubated at room temperature (24° C.) in the dark, for 72 hours, on a shaker at low speed. After 72 hours of incubation, 20 µL of bacteria culture liquid was retrieved from each simulated hub and 10-fold serially diluted. 50 µL of each dilution was spread on LB agar plates and incubated at 37° C. overnight for colony-forming unit (CFU) counting. The simulated hub was also sliced into small pieces and the inside was stained with BacLight Live/Dead staining kit in the dark for 15 minutes to assess the degree of biofilm. Microscopic images were obtained by using a fluorescent microscope with appropriate filter sets (488/520 nm for SYTO-9 and 493/636 nm for propidium iodide.

Figure 16:
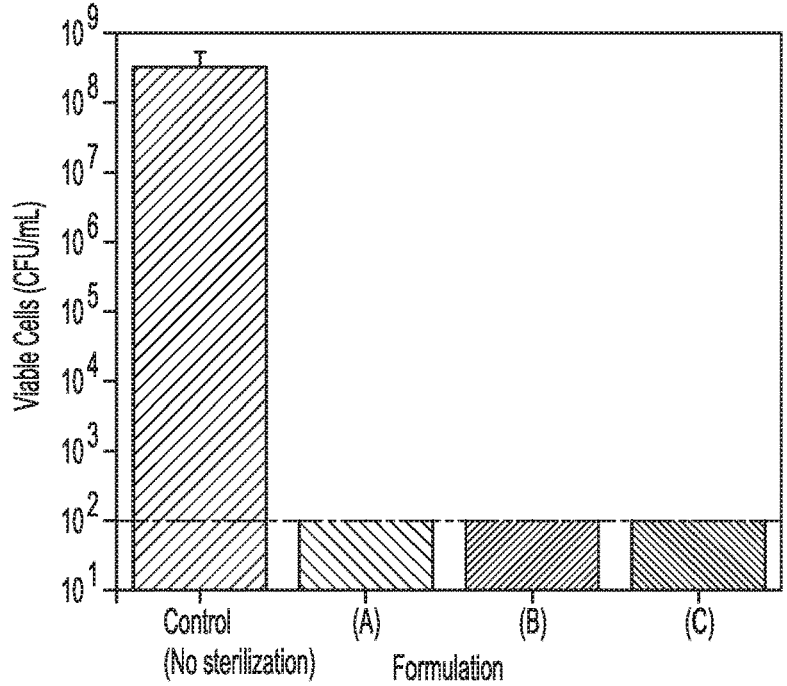
FIG. 16 is a bar graph depicting viable cells (CFU/mL) for a control insert device and three example catheter insert devices (data represents mean±standard deviation, n=3)

Each NO releasing insert formulation (examples A-C) killed all of the bacteria present in the liquid broth of each simulated hub, leading to a 6.4 log reduction of bacteria compared to the control (no NO releasing insert). These results are shown in FIG. 16. This data indicates that examples A-C are capable of killing *S. Aureus* bacteria cells in the liquid broth of a simulated catheter hub region.

Fluorescent microscopic images were taken of the inner lumen wall of each simulated hub and representative black and white reproductions of the originally colored images are pictured in FIGS. 17A through FIG. 17D. The control (FIG. 17A) as well as examples B (FIG. 17C) and C (FIG. 17D) displayed evidence of *S. Aureus* bacteria/biofilm adhered to the inner lumen wall of the simulated hubs. In contrast, example A (FIG. 17B) showed no evidence of significant *S. Aureus* bacteria/biofilm adhesion.

The data from Example A suggests that having a large burst of NO over the first 24 hours is desirable to prevent biofilm formation. Therefore, the formulation of example A (75% GSNO: 25% 30 nm ZnO nanoparticles), was used for additional testing.

Sterilzation and Stability Tests

Prior to animal testing, sterilization of the NO releasing inserts was performed. GSNO naturally reacts to release NO in the presence of light, heat, metal ions, and water. Thus, different sterilization methods were tested to see if they had any negative effects on GSNO stability.

For these tests, additional NO releasing inserts were prepared similarly to example A. Three of these inserts are collectively referred to herein as example E and three others are collectively referred to as example F. The inserts were individually packaged into separate pouches, and sent to the University of Michigan hospital sterilization facility for ethylene oxide (EO) or hydrogen peroxide ($H_2O_2$) treatment.

For EO treatment, the NO releasing inserts (example E) were exposed to a 1 hour preconditioning and humidification process (54° C., 40-80% humidity), followed by 3 hours of exposure to ethylene oxide gas under the same temperature and humidity. Then, a 2 hour ethylene oxide gas evacuation process was performed, followed by 12 hours of air washes.

The $H_2O_2$ treatment (using a STERRAD® system) took approximately 45 minutes total. Under vacuum, 59% (nominal) aqueous $H_2O_2$ was vaporized to cover the NO releasing inserts. Diffusion of the gaseous $H_2O_2$ occurred while the pressure was reduced, which formed low-temperature $H_2O_2$ gas plasma after radio frequency (RF) energy was applied. The generated $H_2O_2$ gas plasma sterilized the NO releasing inserts (example F).

Three control NO releasing inserts (collectively referred to as comp. example G) were prepared similarly to comp. example D, but were not sterilized.

The amount of GSNO on Day 0 was measured for the control inserts (comp. example G). Also on day 0, the remaining NO releasing inserts were sterilized using the EO treatment (example E) or the $H_2O_2$ treatment (example F).

The amount/stability of GSNO within each insert was measured by detecting/quantifying the total amount of NO released using ultraviolet (UV) light and an NOA. Specifically, 2 mL of purified water was added to an NOA sample cell. After a steady baseline was achieved, one of the NO releasing inserts was cut open and the powder filling was transferred into the sample cell using another 2 mL of purified water. An additional 1 mL of purified water was used to rinse all remaining powder on the NOA sample cell walls, down into the bulk solution (total 5 mL of purified water). The GSNO/ZnO containing solution was bubbled with $N_2$ gas at a rate of 50 mL/min to escape from the solution and be carried into the NOA by the $N_2$ sweep gas. UV light was used to irradiate the sample until NO release from GSNO was exhausted, marked by a return to the original baseline. The amount of NO released from each NO releasing insert was directly converted to GSNO because the mole ratio is 1:1. The highest amount of GSNO measured from the three NO releasing control inserts (not sterilized) was assumed to be 100% recovery of GSNO; therefore, all other samples (sterile and non-sterile) were normalized to this value. Thus, >100% GSNO recovery was possible. Table 1 shows the results for example E, example F, and comp. example G (n=3 for each).

Based on these results (lower standard deviation and quicker turn-around), the $H_2O_2$ treatment was selected for further testing.

TABLE 1

| Comp. Example G<br>No Sterilization | Example E<br>$H_2O_2$ Gas 40° C.,<br>30 minutes | Example F<br>EO Gas >80° C.,<br>7 hours |
|---|---|---|
| 98.4% ± 1.6% | 100.2% ± 2.4% | 95.3% ± 10.1% |

Figure 18:
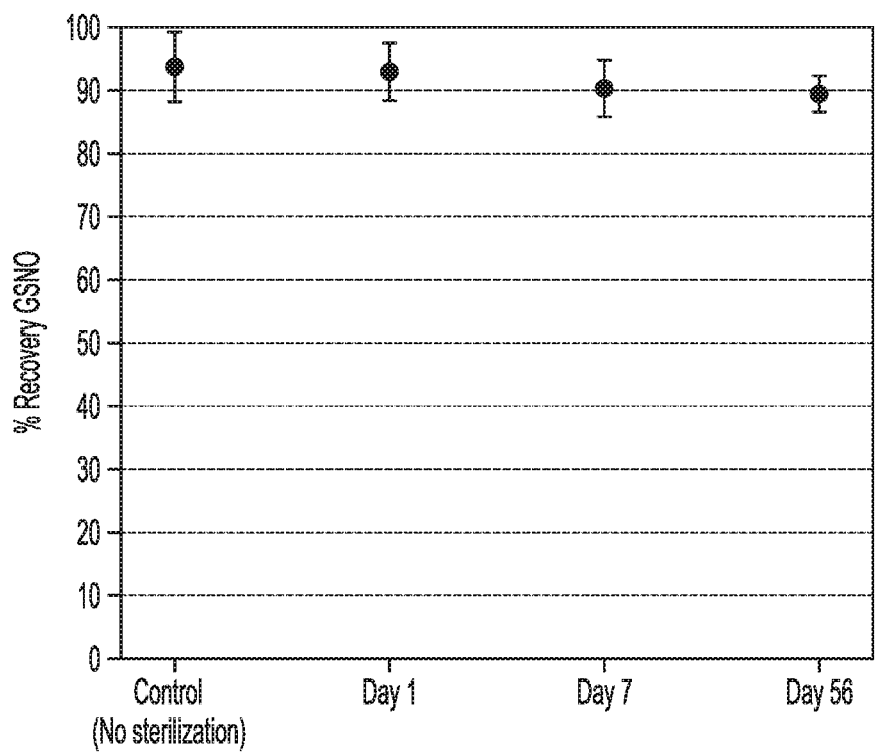
FIG. 18 is a graph depicting the % Recovery of GSNO (Y axis) from a non-sterilized insert device and from an NO releasing insert device on different days (1, 7, and 56) after hydrogen peroxide sterilization (data represents mean±standard deviation, n=3)

The long-term stability of the GSNO inside of the NO releasing inserts was then analyzed. Additional NO releasing inserts were prepared similarly to example A, and were sterilized using the $H_2O_2$ method (collectively referred to as example H). Three of these additional inserts were not sterilized, and were used as a control (collected referred to as comp. example I). The amount of GSNO in each control insert was determined on Day 0 using the method described herein. After $H_2O_2$ sterilization was completed on Day 0 for the remaining inserts (example H), they remained in their individual sterilization pouches and stored in a sealed glass jar with desiccant, in the dark, at room temperature (24° C.) until further use. The GSNO in three of the inserts was measured on Day 1. The GSNO in three other inserts was measured on Day 7. The GSNO in still three other inserts was measured on Day 56. The results are shown in FIG. 18. After nearly 2 months of storage (Day 56), the GSNO inside of the inserts was found to degrade by an average of 4.3%. Therefore, GSNO is relatively stable when stored dry with ZnO nanoparticles inside of the silicone insert devices at room temperature.

Leaching Tests

Tests were performed to determine if any of the powder composition components leak from the insert devices when soaked in solution. Insert devices similar to example A were prepared as described herein, including powder filling through the open end and then sealing the open end. This sealed end of three of insert devices were secured to respective caps of respective test bottles.

For these tests, three control insert devices included only the silicone tubing and the glue adhesive, with no GSNO or ZnO present.

Purified deionized water was used as the soaking solution because the high salt concentration in a saline solution could damage the inductively coupled plasma mass spectrometry (ICP-MS), which was used to detect zinc in the leaching solutions after predetermined periods of soaking.

Two different soaking conditions were used to test for leaching. All of the insert devices were placed into a defined volume (10 mL) of the purified deionized water within test bottles. The three control insert devices and three of the insert devices including the powder composition (collectively referred to as example J) were completely submerged, so that both ends of the insert devices were soaked in the solution within the test bottles. Three other of the insert devices including the powder composition (collectively referred to as example K) was partially submerged in the solution. For partial submersion, the caps with the insert devices secured thereto were used. Because these insert devices were held by the caps of the respective test bottles, the ends sealed after powder composition introduction were not exposed to the solution within the test bottle.

After 24 hours (1 day) of soaking, the insert devices were removed, thoroughly washed, dried, and completely or partially submerged again in fresh purified deionized water. This process was repeated on days 2 and 3. After collection of the respective solutions, the concentration of zinc content in each was measured using ICP-MS. The results are shown in FIG. 19.

Figure 19:
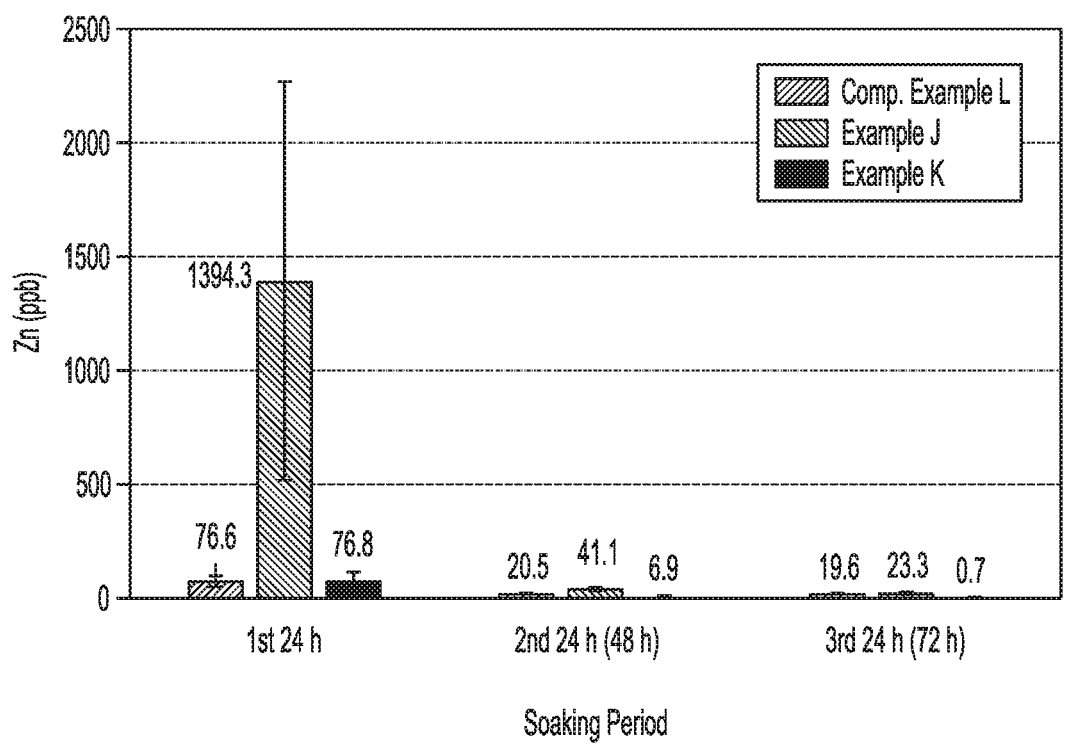
FIG. 19 is a graph depicting Zn leakage (ppb, Y axis) for a control insert device and two example insert devices exposed to different soaking conditions.

As shown in FIG. 19, after the first 24 hour soaking period, the concentration of zinc detected in the solution for the two different soaking conditions were extremely different (1394.3 ppb for example J (complete submersion) vs. 76.8 ppb for example K (partial submersion)). As noted above, the difference between the two soaking methods was that, with complete submersion, the end of the silicone tube that was sealed after filling with the GSNO/ZnO powder was directly exposed to the solution; whereas, with partial submersion, this end was inside of the cap and not exposed to solution. Thus, a conclusion can be made that ZnO was able to creep out of the end of the silicone tubing that was sealed on the second end because that end of the tubing was directly exposed to the ZnO before sealing (e.g., during filling), whereas the other end of the silicone tubing was pre-sealed and dried before any exposure to ZnO (creating a more solid seal). Moreover, the large error bar for example K (insert device that were completely submerged), indirectly demonstrates this phenomenon because the amount of ZnO that could be close to the edge of the second sealed end could vary immensely because the inserts were made by hand.

Overall, the data in FIG. 19 demonstrated that zinc was not leaching out from the walls of the silicone tubing of the NO releasing insert devices.

In Vitro Catheter Hub Tests

NO releasing inserts were prepared in the same manner as example A and were pre-sterilized by the $H_2O_2$ sterilization method. The antimicrobial efficacy of these NO insert devices in real hemodialysis catheter hubs were tested against gram-positive and gram-negative strains, *S. Aureus*, and *P. Aeruginosa*, respectively.

The catheters utilized for this test were 28 cm long PERMCATH™ Pediatric Silicone Chronic Dual Lumen Oval Catheters (from Covidien/Medtronic). The clamp on the catheter's hub region was clamped shut and 0.3 mL of overnight grown bacteria cultures (1×108 CFU/mL) in 10% LB broth was added. An NO releasing insert was inserted inside of the catheter hub and sealed with a cap.

For control samples, no NO releasing insert was added.

Each catheter was incubated at room temperature (24° C.) in the dark, for 72 hours, on a shaker at low speed. After 72 hours of incubation, 20 µL of bacteria culture liquid was retrieved from each hub region and 10-fold serially diluted. 50 µL of each dilution was spread on LB agar plates and incubated at 37° C. overnight for colony-forming unit (CFU) counting. Compared to the control insert, the example inserts led to a log reduction of 6.6 and 6.7 against *S. Aureus* and *P. Aeruginosa*, respectively. This data suggests that the NO releasing inserts containing the formulation of example A (75% GSNO/25% ZnO nanoparticles) are extremely effective at killing both gram-positive and gram-negative strains.

In Vivo—Sheep Tests
General Procedures

Each of these tests involved animal handling and surgical procedures that were approved by the University of Michigan Committee on Use and Care of Animals (24 hours of fasting and pre-surgical analgesia with Fentanyl transdermal patch 100 pg/h) in accordance with university and federal regulations.

Adult sheep weighing 45-50 kg were utilized. Under general anesthesia, 28 cm long (13 cm cuff to proximal tip) PERMCATH™ Pediatric Silicone Chronic Dual Lumen Oval Catheters were placed using the Seldinger wire technique in the right and left jugular veins (from about 3 cm to about 5 cm above the subclavian), aiming to place the proximal tip in the RA-SVC junction. Caution was taken not to expose or manipulate the vessels. Catheters were secured to the skin and covered with a sterile dressing. After catheter placements, the sheep were recovered from anesthesia and housed in a barn (non-sterile conditions).

All catheters were capped and filled with 2,000 U heparinized saline solution (2 mL) injected via the distal end of the lumen. The NO releasing inserts used for the sheep tests were made using the formulation in example A: 75% GSNO: 25% 30 nm size ZnO nanoparticles. The NO releasing inserts were attached to male luer lock injection site caps (Qosina), using the DOWSIL® adhesive glue, and allowed to dry for 24 hours. Each NO releasing insert cap was individually packaged and sterilized using the $H_2O_2$ sterilization described herein. The sterile NO releasing insert caps were stored at room temperature (24° C.) and shielded from light until they were used.

Prior to necropsy (day 14 of each test), 10,000 U bolus of heparin was given via a cephalic vein angiocath, followed by FatalPlus IV injection. Each catheter was procured using sterile techniques. The external surface of each catheter was sterilized by wiping with a 70% ethanol solution. One cm length sections were cut from each section of catheter. Each section was homogenized in 2 mL of 1× PBS (10 mM, pH 7.2) in a 15-mL tube using a homogenizer (OMNI TH, OMNI International, Kennesaw, GA) at full speed to remove all bacteria/biofilm adhered to the inner lumen walls, and a designated amount (e.g., 20 µL) of the resulting solution was 10-fold serially diluted. A designated amount of each dilution (e.g., 5 µL) was spread on LB agar plates and incubated at 37° C. overnight for CFU counting.

Additionally, >0.5 cm length sections were cut from each section of catheter, and the inner lumen surfaces were stained with BacLight Live/Dead staining kit in the dark for 15 minutes. Microscopic images were obtained by using a fluorescent microscope with appropriate filter sets (488/520 nm for SYTO-9 and 493/636 nm for propidium iodide.

Figure 20:
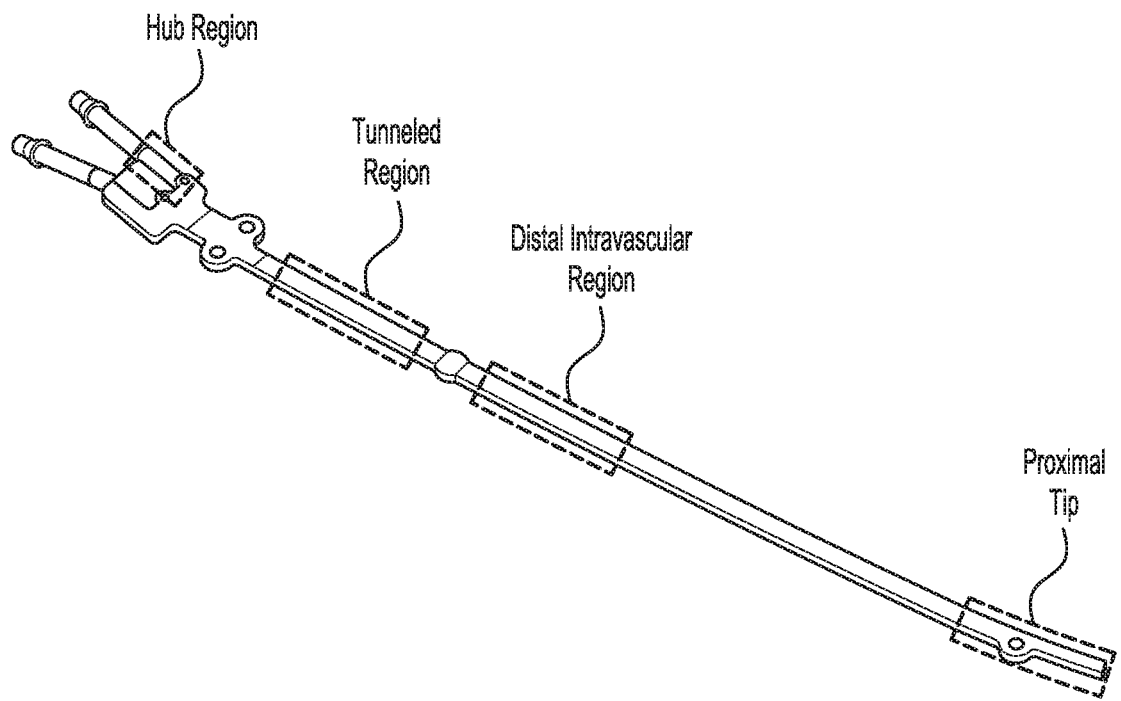
FIG. 20 is a schematic illustration of a catheter and the different regions tested for bacteria/biofilm formation.

FIG. 20 is a schematic illustration of the catheters used in the sheep tests, as well as the various regions that were examined. The regions included the hub region, the tunneled region, the distal intravascular region, and the proximal tip.

Sheep Test #1

Figure 21:
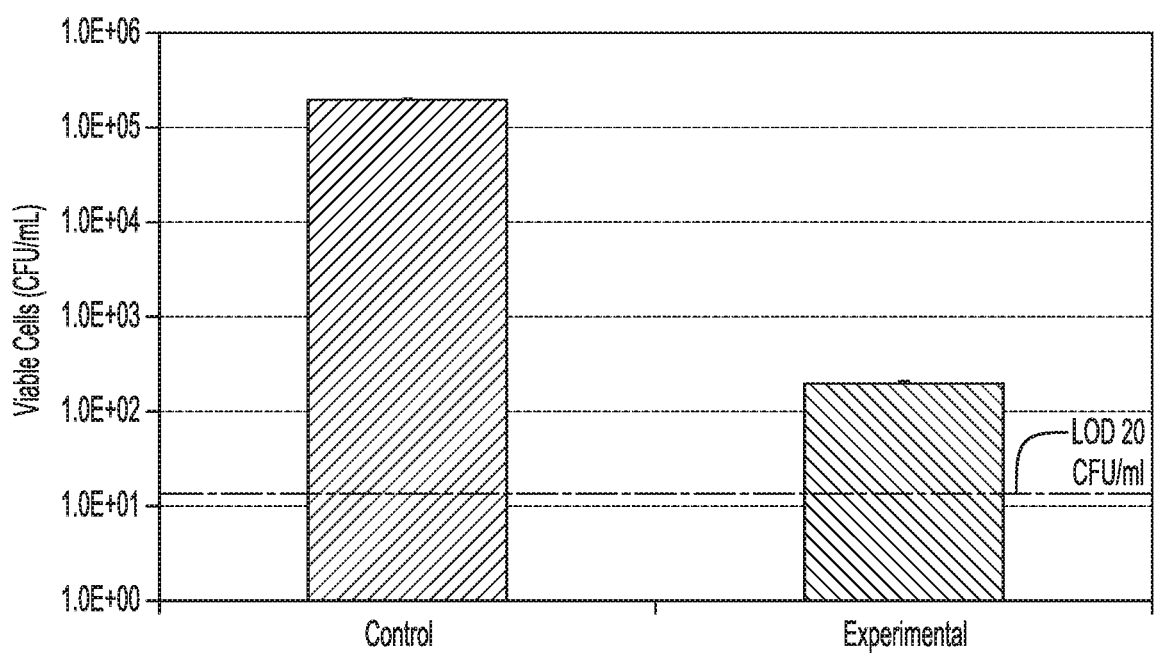
FIG. 21 is a bar graph depicting viable cells (CFU/mL) for control insert devices and experimental catheter insert devices (data represents mean±standard deviation, n=4)

Two adult sheep were studied during Sheep Test #1. One sheep (comp. example sheep 1) was designated as a control (n=4 catheter hubs total, no NO releasing inserts) and the other sheep (example sheep 2) was designated as experimental (n=4 catheter hubs total, using NO releasing insert caps). On postoperative days 0, 2, 4, 7, 9, 11, and 14, the caps were changed. For this procedure, 3.5 mL of blood were drawn from each lumen, the lumens were then locked with 2,000 U heparinized saline solution (2 mL), and both NO releasing insert caps and control caps were replaced with new caps, respectively. On postoperative day 14, 50 µL of liquid from the hub region of each catheter lumen was taken and spread on LB agar plates. The plates were incubated at 37° C. overnight for colony-forming unit (CFU) counting. The results are shown in FIG. 21. As depicted, the catheters of example sheep 2, which were treated with the insert devices, has a >3 log unit reduction in viable cells when compared to the catheters of comp. sheep 1, which were not treated with any insert device.

Fluorescent microscopic images were taken of the inner lumen walls of the hub, tunneled, and distal regions of the catheters using Live/Dead dye stain. In the original colored images, green staining depicted live bacteria and red depicted dead bacteria.

Figure 22A:
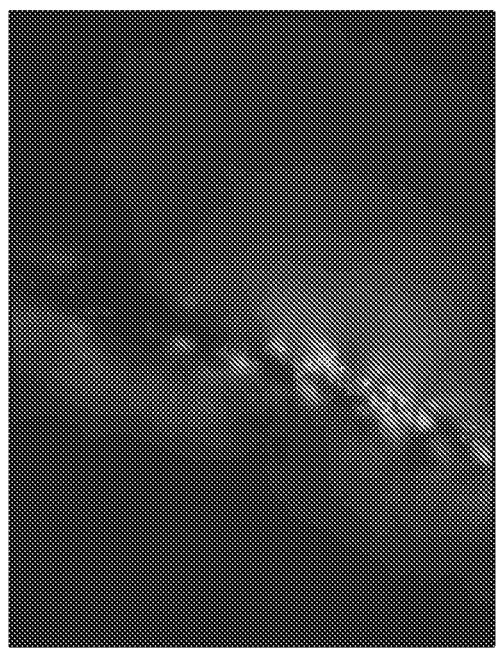
FIGS. 22A and 22B are black and white reproductions of originally colored fluorescent microscopy images depicting a hub region of a control catheter (in comp. sheep 1) that was not treated with an insert device (FIG. 22A) and of an example catheter (in example sheep 2) that was treated with an insert device (FIG. 22B), where green staining depicted live bacteria and red (not readily visible) depicted dead bacteria.
Figure 22B:
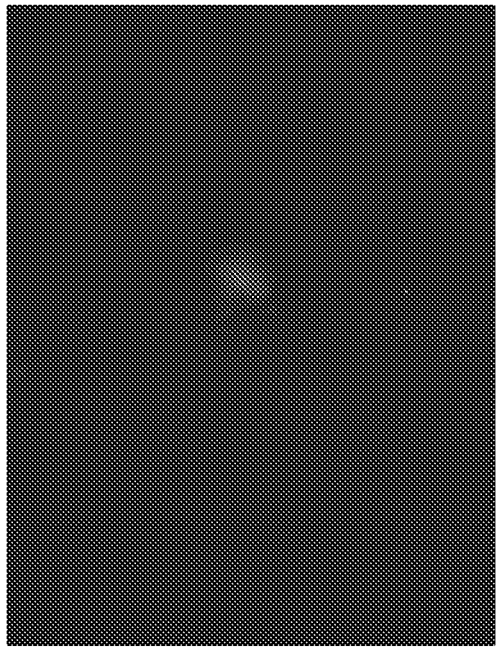

FIGS. 22A and 22B respectively depict (in black and white) the fluorescent microscopic images of the hub region of one of the catheters from comp. example sheep 1 and of the hub region of one of the catheters from example sheep 2. The hub region of the catheter from comp. example sheep 1 had a biofilm of live bacteria, whereas the hub region of the catheter from example sheep 2 had minimal single cells (dead or alive).

Figure 23A:
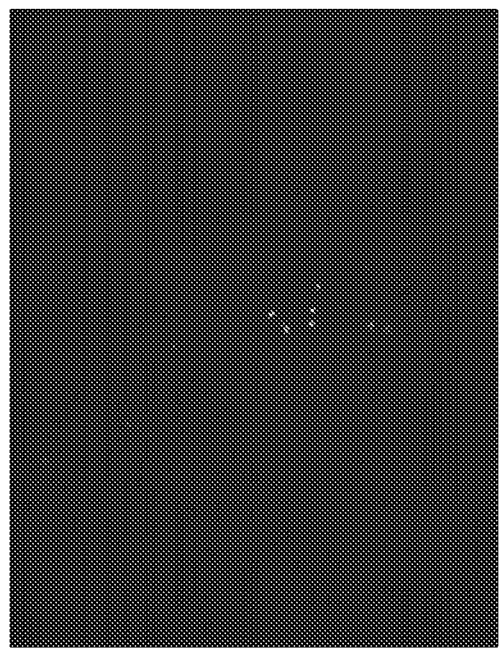
FIGS. 23A and 23B are black and white reproductions of originally colored fluorescent microscopy images depicting a tunneled region of a control catheter (in comp. sheep 1) that was not treated with an insert device (FIG. 23A) and of an example catheter (in example sheep 2) that was treated with an insert device (FIG. 23B), where green staining depicted live bacteria and red (not readily visible) depicted dead bacteria.
Figure 23B:
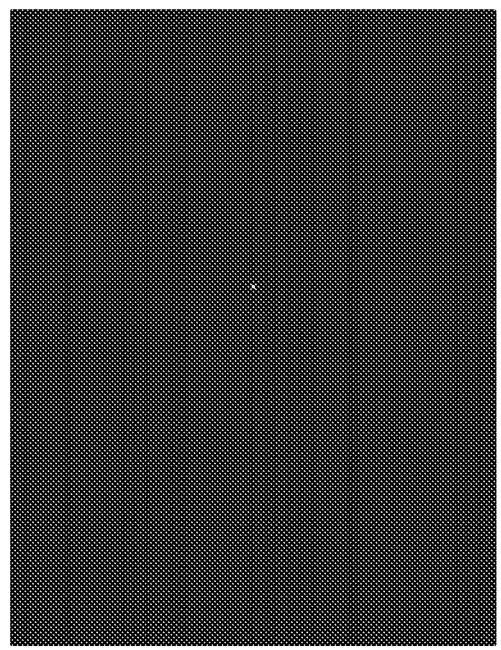

FIGS. 23A and 23B respectively depict (in black and white) the fluorescent microscopic images of the tunneled region of one of the catheters from comp. example sheep 1 and of tunneled hub region of one of the catheters from example sheep 2. The tunneled region of the catheter from comp. example sheep 1 had multiple single cells of live bacteria, whereas the tunneled region of the catheter from example sheep 2 had minimal single cells (dead or alive).

Figure 24A:
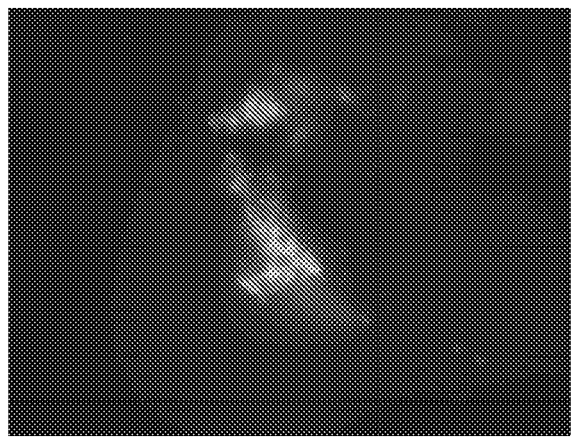
FIGS. 24A and 24B are black and white reproductions of originally colored fluorescent microscopy images depicting a distal tip of a control catheter (in comp. sheep 1) that was not treated with an insert device (FIG. 24A) and of an example catheter (in example sheep 2) that was treated with an insert device (FIG. 24B), where green staining depicted live bacteria and red (not readily visible) depicted dead bacteria.
Figure 24B:
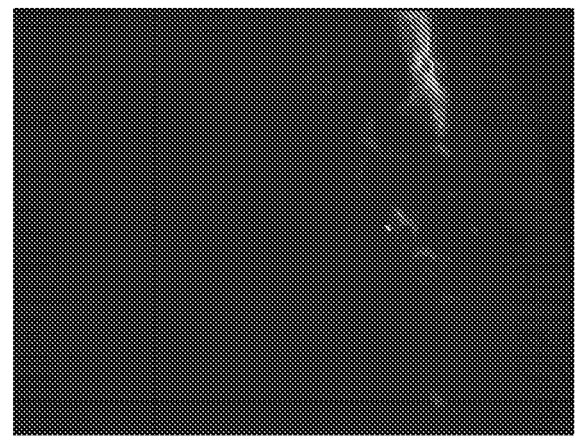

FIGS. 24A and 24B respectively depict (in black and white) the fluorescent microscopic images of the distal tip of one of the catheters from comp. example sheep 1 and of the distal tip of one of the catheters from example sheep 2. The distal tip of the catheter from comp. example sheep 1 had a biofilm of live and dead bacteria. The colored version of FIG. 24B (of the distal tip of the catheter from example sheep 1) exhibited some red and green. However, it was determined from higher magnified images, that these red and green striations were from the surface texture, not from bacteria. In fact, the distal tip of the catheter from example sheep 2 had minimal single cells (dead or alive).

Sheep Test #2

Two adult sheep were studied during Sheep Test #2. One sheep (comp. example sheep 3) was designated as control (n=4 catheter hubs total, no NO releasing inserts) and the other sheep (example sheep 4) was designated as experimental (n=4 catheter hubs total, using NO releasing insert caps). On postoperative days 0, 2, 4, 7, 9, 11, and 14, 50 µL of liquid from the hub region of each catheter lumen was taken for CFU counting. Then, 3.5 mL of blood was drawn from each lumen, the lumens were then locked with 2,000 U heparinized saline solution (2 mL), and both NO releasing insert caps and control caps were replaced with new caps, respectively. The control and experimental caps were changed every 2 to 3 days and blood was drawn through each lumen to simulate the average time between dialysis treatments and blood exposure. After 14 days, the test was terminated and each hemodialysis catheter was evaluated for the amount of bacteria/biofilm present on the inside wall of four separate regions of the catheter (FIG. 20).

Figure 25:
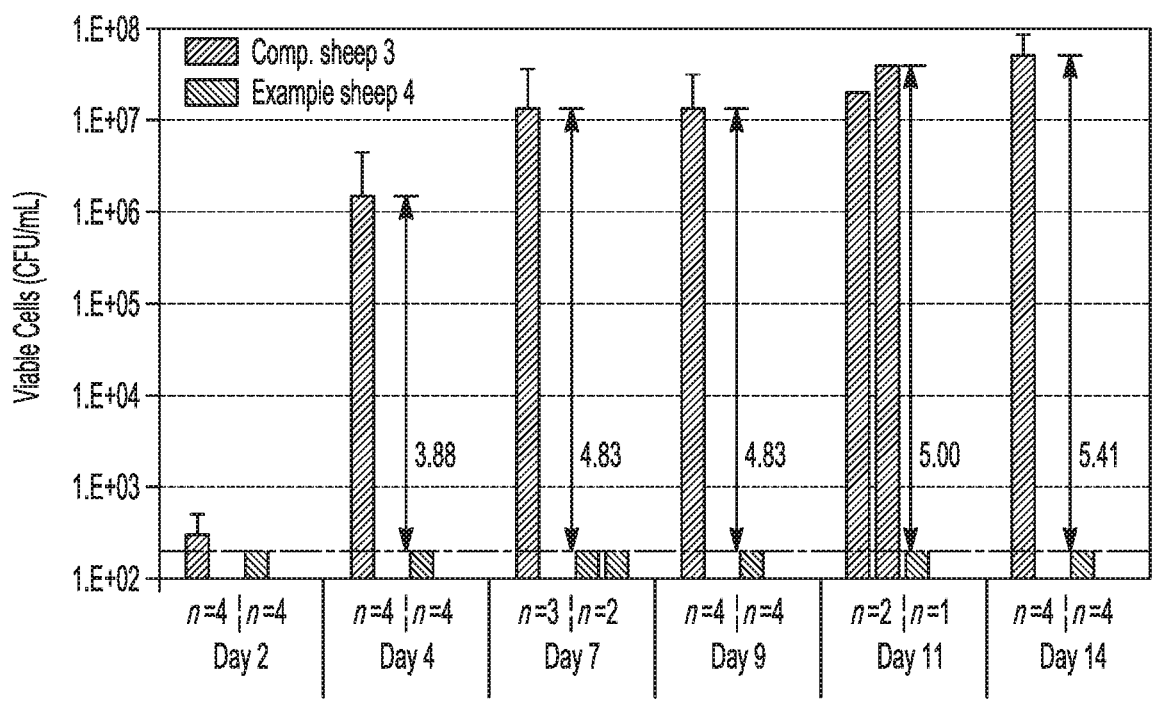
FIG. 25 is a bar graph depicting viable cells (CFU/mL) for control insert device caps (in comp. sheep 3) and experimental insert device caps (in example sheep 4) (data represents mean±standard deviation, n varied on some days)

For CFU counting, 20 μL (of the 50 μL) was 10-fold serially diluted with PBS buffer. 5 μL of each dilution was transferred onto an LB agar plate and the plate was incubated overnight for colony counting. The results of the bacteria counts taken from the liquids within the hub region every 2-3 days are summarized in FIG. 25. On particular days, such as days 7 and 11, some unforeseen circumstances prevented a proper liquid sample from being obtained from each hub region. However, the data remained consistent where comp. sheep 3 (with no NO releasing insert caps in the catheters) displayed significant bacteria counts after day 4, and example sheep 4 (with NO releasing insert caps in the catheters) showed no bacteria on any day, therefore reaching the limit of detection (220 CFU/mL, identified by the dashed line in FIG. 25) after each day of testing. A log reduction of 3.88 was already observed by day 4 and increased to 5.42 by day 14 for example sheep 4 versus comp. example sheep 3. This data suggests that the NO releasing insert caps have a significant antimicrobial effect against bacteria present in the liquid of the hub region under real world conditions.

Figure 26:
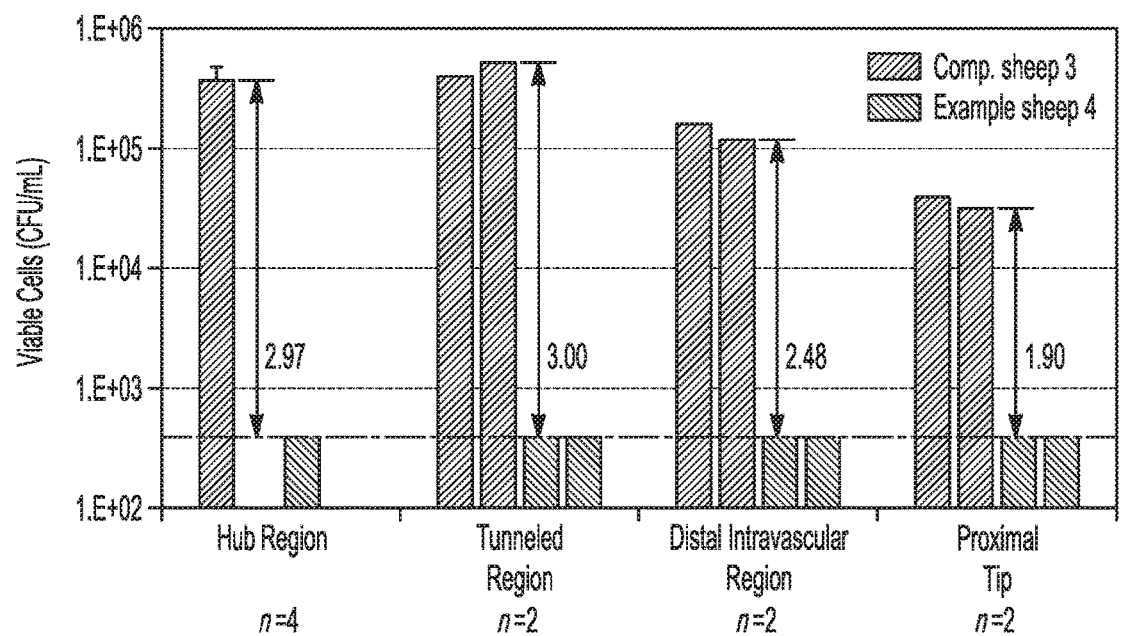
FIG. 26 is a bar graph depicting viable cells (CFU/segment) for different regions of control insert device caps (in comp. sheep 3) and experimental insert device caps (in example sheep 4) (data represents mean±standard deviation, n varied for each segment)

Upon completion of the 14 day study, the four regions of each catheter (shown in FIG. 20) were tested for bacteria/biofilm adhered to the inner lumen walls. This test was conducted by first sterilizing the outside of the catheter, cutting out the specific sections, and using a homogenizer to remove all of the adhered bacteria/biofilm from the inner lumen wall for bacteria enumeration (as described above). The results of this test are summarized in FIG. 26. For the catheters from comp. sheep 3, all four regions of the catheters had a significant amount of bacteria/biofilm present. For catheters from example sheep 4 (with the experimental NO releasing insert caps), no bacteria was detected in any of the four regions. Interestingly, bacteria/biofilm prevention was observed in all regions of the catheter and not just the hub region (where the NO is locally released). This data quantitatively suggests that bacteria can migrate to the proximal regions of the catheter from the hub region and that the NO releasing insert caps have significant antibacterial/anti-biofilm potential throughout all regions of a catheter during a real world situation.

Fluorescent microscopic images were taken of the inner lumen walls of each region of the catheters using Live/Dead dye stain. In the original colored images, green staining depicted live bacteria and red depicted dead bacteria.

Figure 27A:
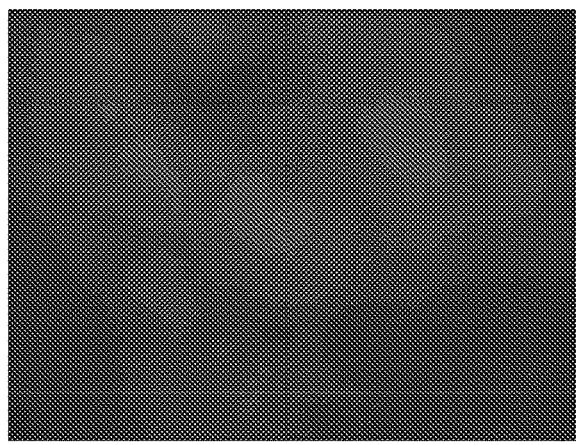
FIGS. 27A and 27B are black and white reproductions of originally colored fluorescent microscopy images depicting a hub region of a control catheter (in comp. sheep 3) that was not treated with an insert device (FIG. 27A) and of an example catheter (in example sheep 4) that was treated with an insert device (FIG. 27B), where green staining depicted live bacteria and red (not readily visible) depicted dead bacteria.
Figure 27B:
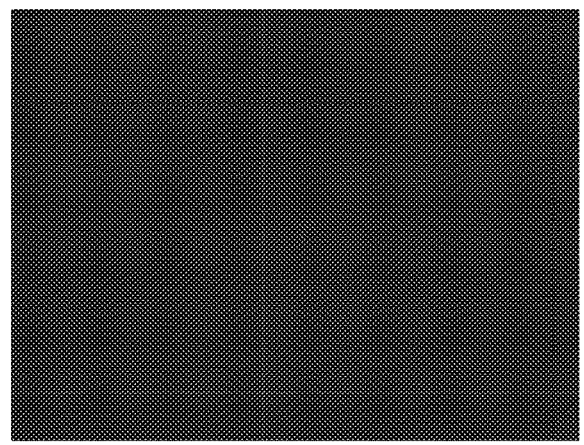

FIGS. 27A and 27B respectively depict (in black and white) the fluorescent microscopic images of the hub region of one of the catheters from comp. example sheep 3 and of the hub region of one of the catheters from example sheep 4. The hub region of the catheter from comp. example sheep 3 had a biofilm of live bacteria, whereas the hub region of the catheter from example sheep 4 had minimal single cells (dead or alive).

Figure 28A:
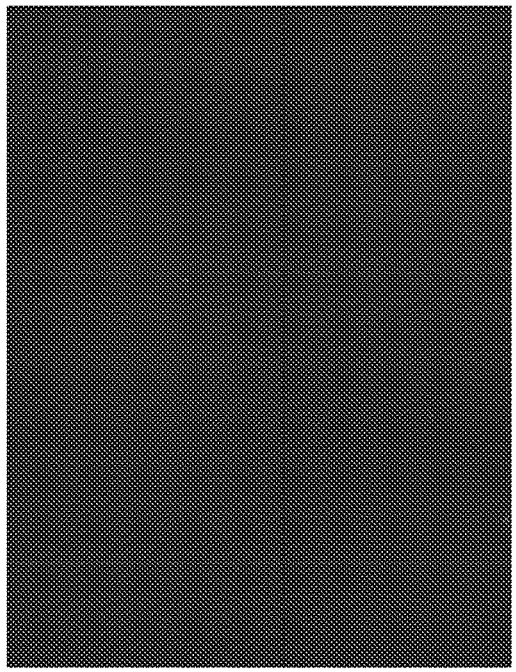
FIGS. 28A and 28B are black and white reproductions of originally colored fluorescent microscopy images depicting a tunneled region of a control catheter (in comp. sheep 3) that was not treated with an insert device (FIG. 28A) and of an example catheter (in example sheep 4) that was treated with an insert device (FIG. 28B), where green staining depicted live bacteria and red (not readily visible) depicted dead bacteria.
Figure 28B:
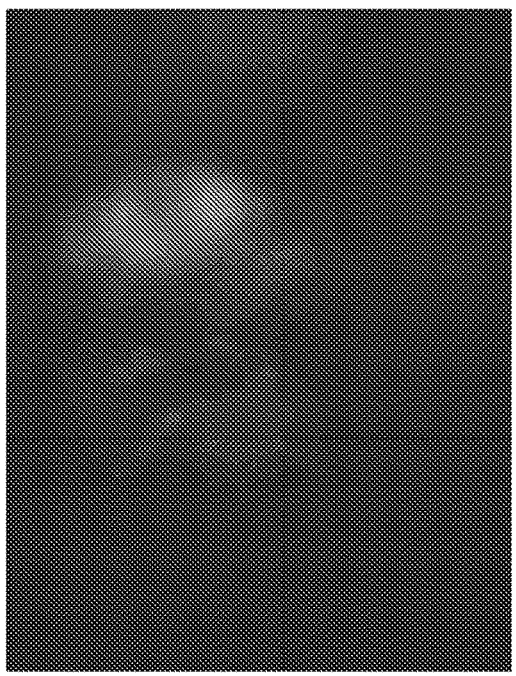

FIGS. 28A and 28B respectively depict (in black and white) the fluorescent microscopic images of the tunneled region of one of the catheters from comp. example sheep 3 and of tunneled hub region of one of the catheters from example sheep 4. The tunneled region of the catheter from comp. example sheep 3 had a biofilm of live bacteria, whereas the tunneled region of the catheter from example sheep 4 had minimal single cells (dead or alive).

Figure 29A:
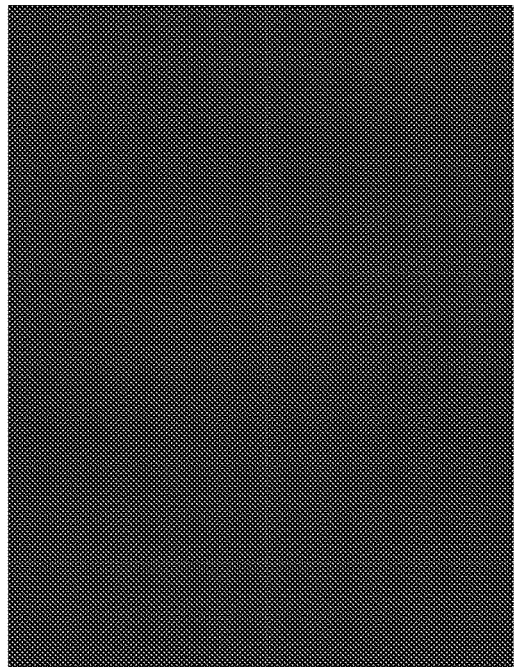
Figure 29B:
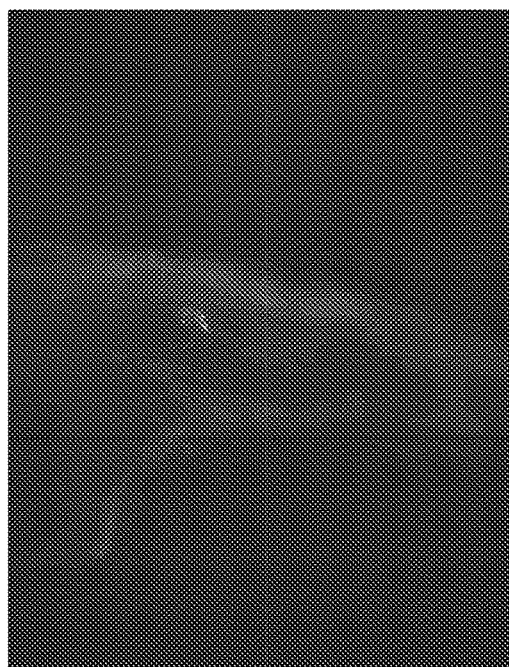

FIGS. 29A and 29B respectively depict (in black and white) the fluorescent microscopic images of the distal intravascular region of one of the catheters from comp. example sheep 3 and of the distal intravascular region of one of the catheters from example sheep 4. The distal intravascular region of the catheter from comp. example sheep 3 had a biofilm of live and dead bacteria. The distal intravascular region of the catheter from example sheep 4 had minimal single cells (dead or alive).

Figure 30A:
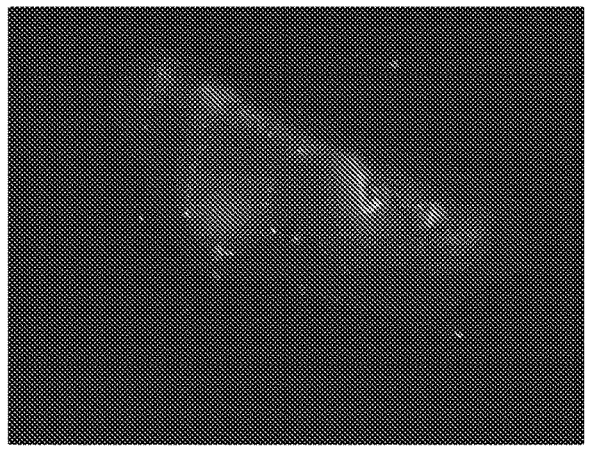
FIGS. 30A and 30B are black and white reproductions of originally colored fluorescent microscopy images depicting a distal tip of a control catheter (in comp. sheep 3) that was not treated with an insert device (FIG. 30A) and of an example catheter (in example sheep 4) that was treated with an insert device (FIG. 30B), where green staining depicted live bacteria and red (not readily visible) depicted dead bacteria.
Figure 30B:
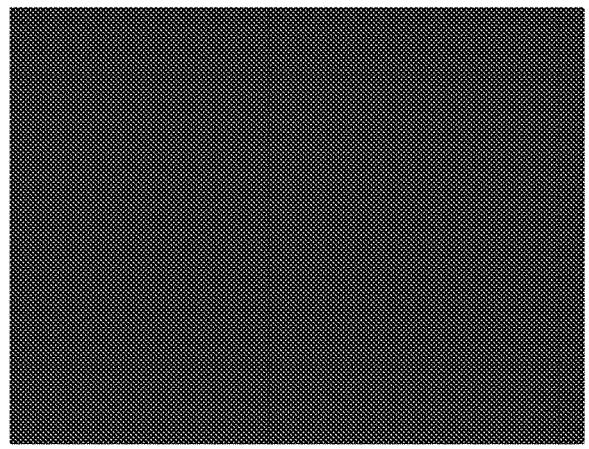

FIGS. 30A and 30B respectively depict (in black and white) the fluorescent microscopic images of the distal tip of one of the catheters from comp. example sheep 3 and of the distal tip of one of the catheters from example sheep 4. The distal tip of the catheter from comp. example sheep 3 had a biofilm of live and dead bacteria. The distal tip of the catheter from example sheep 4 had minimal single cells (dead or alive).

This data qualitatively suggests that the NO releasing insert caps prevent bacteria/biofilm formation in each catheter region under real world conditions.

Sheep Test #3

Two adult sheep were studied during Sheep Test #3. In this test, a commercially available antimicrobial cap with chlorhexidine as the antimicrobial agent was used for comparison.

For sheep 5, the catheter implanted in the right jugular vein was designated for the commercial chlorhexidine caps and the catheter implanted in the left jugular vein was designated for the NO release insert caps. For sheep 6, the designations were reversed such that right jugular vein was designated for the NO release insert caps and the catheter implanted in the left jugular vein was designated for the chlorhexidine caps. In total, for chlorhexidine caps there were n=4 catheter hubs and for the NO releasing insert caps there were also n=4 catheter hubs. On postoperative days 0, 2, 3, 6, 8, 10, 12, and 14, 50 μL of liquid from the hub region of each catheter lumen was taken for CFU counting. Then, 3.5 mL of blood were drawn from each lumen, locked with 2,000 U heparinized saline solution (2 mL), and both NO releasing insert caps and chlorhexidine caps were replaced with new caps, respectively.

Figure 31:
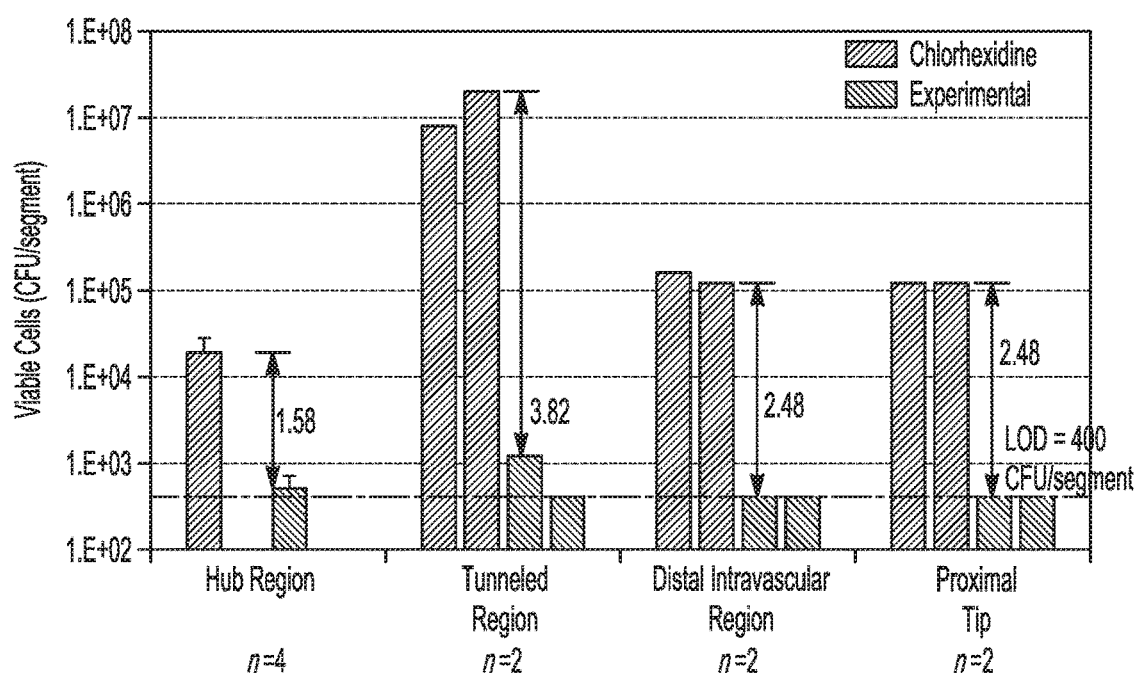
FIG. 31 is a bar graph depicting viable cells (CFU/segment) for different regions of comparative device caps (with chlorhexidine) and experimental insert device caps (with the NO releasing formulation) (data represents mean±standard deviation, n varied for each segment)

After 14 days, the test was terminated and each hemodialysis catheter was evaluated for the amount of bacteria/biofilm present on the inside wall of four separate regions of the catheter (FIG. 20). This test was conducted by first sterilizing the outside of the catheter, cutting out the specific sections, and using a homogenizer to remove all of the adhered bacteria/biofilm from the inner lumen wall for bacteria enumeration (as described above). The results of this test are summarized in FIG. 31. For the experimental catheters, minimal bacteria were detected in the hub and tunneled regions and no bacteria were detected in the distal intravascular region and proximal tip. For the chlorhexidine catheters, bacteria/biofilm was detected in all four regions. The tunneled region of the catheter had the largest log reduction of bacteria (3.82) for the experimental versus chlorhexidine catheters. Overall, this data suggests that the NO releasing insert caps are much more capable of preventing bacteria/biofilm formation in all four regions of a hemodialysis catheter compared to commercially available chlorhexidine caps.

Fluorescent microscopic images were taken of the inner lumen walls of each region of the catheters using Live/Dead dye stain. In the original colored images, green staining depicted live bacteria and red depicted dead bacteria.

Figure 32A:
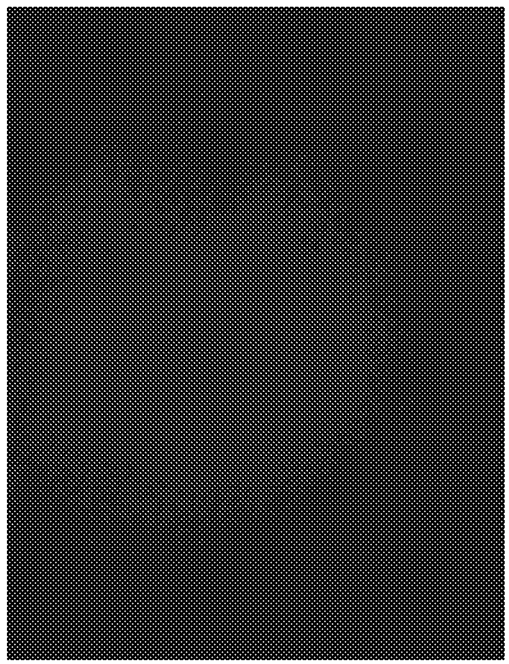
FIGS. 32A and 32B are black and white reproductions of originally colored fluorescent microscopy images depicting a hub region of a comparative catheter that was treated with a comparative device cap (FIG. 32A) and of an example catheter that was treated with an example insert device (FIG. 32B), where green staining depicted live bacteria and red (not readily visible) depicted dead bacteria.
Figure 32B:
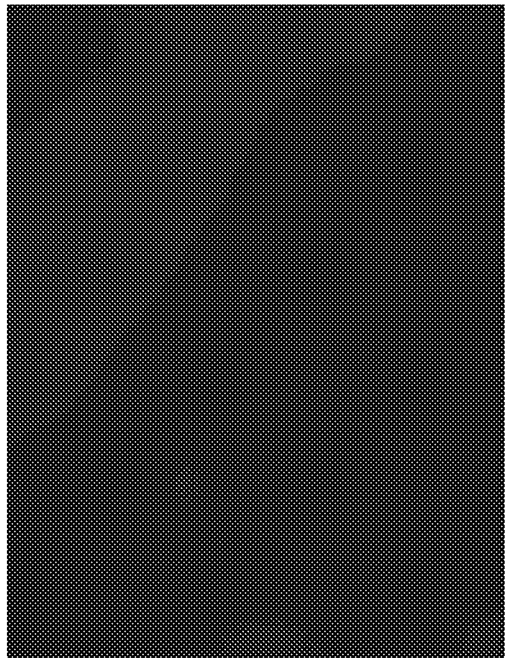

FIGS. 32A and 32B respectively depict (in black and white) the fluorescent microscopic images of the hub region of one of the chlorhexidine catheters and of the hub region of one of the experimental catheters. The hub regions both had minimal single cells (dead or alive).

Figure 33A:
FIGS. 33A and 33B are black and white reproductions of originally colored fluorescent microscopy images depicting a tunneled region of a comparative catheter that was treated with a comparative device cap (FIG. 33A) and of an example catheter that was treated with an example insert device (FIG. 33B), where green staining depicted live bacteria and red (not readily visible) depicted dead bacteria.
Figure 33B:
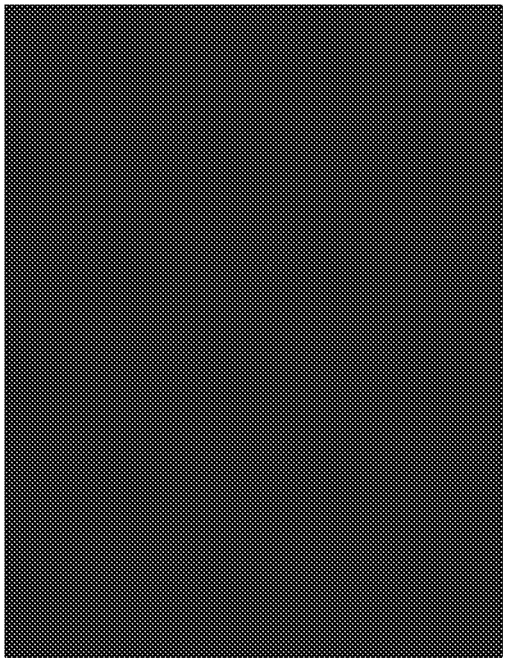

FIGS. 33A and 33B respectively depict (in black and white) the fluorescent microscopic images of the tunneled region of one of the chlorhexidine catheters and of the tunneled region of one of the experimental catheters. The tunneled region of the chlorhexidine catheter had a biofilm of live bacteria, whereas the tunneled region of the experimental catheter had minimal single cells (dead or alive).

Figure 34A:
FIGS. 34A and 35B are black and white reproductions of originally colored fluorescent microscopy images depicting a distal intravascular region of a comparative catheter that was treated with a comparative device cap (FIG. 34A) and of an example catheter that was treated with an example insert device (FIG. 34B), where green staining depicted live bacteria and red (not readily visible) depicted dead bacteria.
Figure 34B:

FIGS. 34A and 34B respectively depict (in black and white) the fluorescent microscopic images of the distal intravascular region of one of the chlorhexidine catheters and of the distal intravascular region of one of the experimental catheters. The distal intravascular region of the chlorhexidine catheter had a biofilm of live and dead bacteria. The distal intravascular region of the experimental catheter had minimal single cells (dead or alive).

Figure 35A:
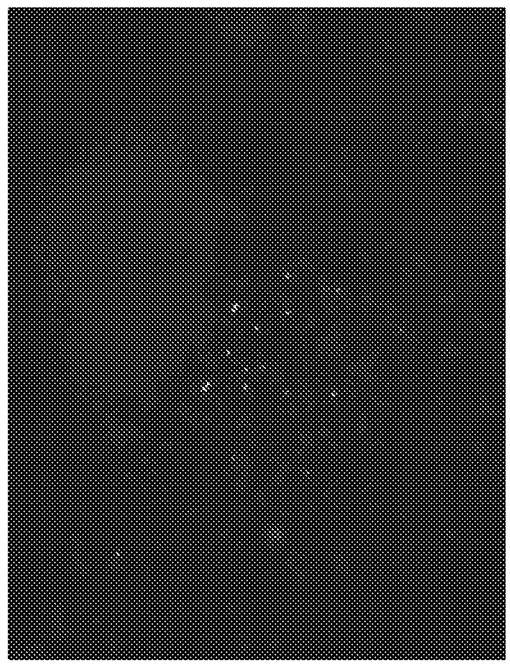
Figure 35B:
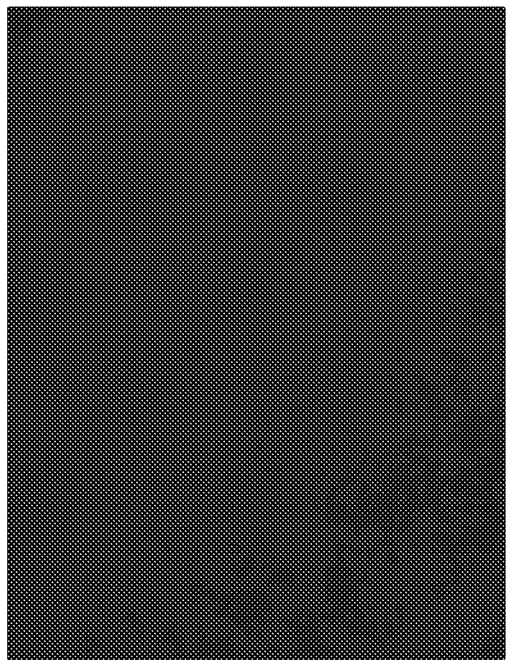

FIGS. 35A and 35B respectively depict (in black and white) the fluorescent microscopic images of the distal tip of one of the chlorhexidine catheters and of the distal tip of one of the experimental catheters. The distal tips of the chlorhexidine catheter and of the experimental catheter each had minimal single cells (dead or alive).

The chlorhexidine catheters displayed significant bacteria/biofilm adhered to the inner lumen wall of the tunneled region, which corresponds to the elevated bacteria/biofilm counts obtained from the tunneled region. The experimental catheters (NO releasing insert caps) displayed minimal to no bacteria adhered to the inner lumen walls of all four regions. This data indicates that the NO releasing insert cap prevents more bacteria/biofilm formation in each catheter region compared to the commercially available chlorhexidine cap.

It is to be understood that the ranges provided herein include the stated range and any value or sub-range within the stated range, as if the value(s) or sub-range(s) within the stated range were explicitly recited. For example, a range from about 1 nm to about 900 nm should be interpreted to include not only the explicitly recited limits of from about 1 nm to about 900 nm, but also to include individual values, such as about 3.7 nm, about 45 nm, about 100 nm, about 520.5 nm, 650 nm, 799 nm, etc., and sub-ranges, such as from about 395 nm to about 595 nm, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A catheter insert device, comprising:
   a powder composition including a solid phase S-nitrosothiol (RSNO);
   a housing, including:
     a polymeric wall that is i) permeable to nitric oxide, ii) non-porous, and iii) permeable to water vapor; and
     an inner lumen defined at least in part by the polymeric wall;
   wherein the powder composition is completely sealed within the inner lumen of the housing; and
   a solid phase additive completely sealed within the inner lumen of the housing, wherein the solid phase additive is a metal wire.

2. The catheter insert device as defined in claim 1 wherein the powder composition further comprises a water uptake material selected from the group consisting of poly(ethylene glycol), poly(vinyl alcohol), a polypeptide, a polyionic species, a monosaccharide, a polysaccharide, silica particles, and a salt.

3. The catheter insert device as defined in claim 2 wherein a weight ratio of the solid phase RSNO to the water uptake material ranges from 1:1 to 10:1.

4. The catheter insert device as defined in claim 3, wherein the powder composition further comprises an additional solid phase additive to accelerate a rate of release of nitric oxide from the solid phase RSNO after exposure to water vapor.

5. The catheter insert device as defined in claim 4 wherein the powder composition includes from about 40 wt % to about 85.5 wt % of the solid phase RSNO, from about 5 wt % to about 20 wt % of the additional solid phase additive, and from about 8 wt % to about 47.5 wt % of the water uptake material.

6. The catheter insert device as defined in claim 1 wherein:
   the powder composition further comprises an additional solid phase additive to accelerate a rate of release of nitric oxide from the solid phase RSNO after exposure to water vapor; and
   the additional solid phase additive is selected from the group consisting of zinc oxide nanoparticles, a copper (II/I)-ligand complex, copper nanoparticles, ascorbic acid, a thiol, a hydrogen ion precursor, a selenium species, an organo-selenium molecule, an organo-tellurium molecule, stainless steel nanoparticles, gold nanoparticles, silica or polymeric particles coated with or possessing immobilized forms of an organic accelerant species, and combinations thereof.

7. The catheter insert device as defined in claim 6 wherein the powder composition consists of from about 15 wt % to about 95 wt % of the solid phase RSNO and from about 5 wt % to about 85 wt % of the additional solid phase additive.

8. The catheter insert device as defined in claim 1 wherein the polymeric wall is selected from the group consisting of silicone rubber, polyurethane, polyethylene, plasticized poly(vinyl chloride) (PVC), siloxane-based polyurethane elastomers, and thermoplastic silicone-polycarbonate-polyurethane.

9. The catheter insert device as defined in claim 1 wherein the polymeric wall is a tube, and wherein the housing further comprises respective sealing members attached to opposed ends of the tube.

10. A kit, comprising:
    a catheter insert device, including:
      a powder composition including a solid phase S-nitrosothiol (RSNO);
      an insert housing, including:
        a polymeric wall that is i) permeable to nitric oxide, ii) non-porous, and iii) permeable to water vapor; and an inner lumen defined at least in part by the polymeric wall;
wherein the powder composition is completely sealed within the inner lumen of the housing; and
a catheter, including:
a catheter tubing that is permeable to nitric oxide and has at least one lumen; and
an adapter attached to a proximal end of the catheter tubing and having an opening that is operatively connected to the at least one lumen of the catheter tubing; and
a mechanism to lock the catheter insert device in place within the at least one lumen or within the adapter.

11. The kit as defined in claim 10 wherein the powder composition further comprises a water uptake material selected from the group consisting of poly(ethylene glycol), poly(vinyl alcohol), a polypeptide, a polyionic species, a monosaccharide, a polysaccharide, silica particles, and a salt.

12. The kit as defined in claim 11 wherein a weight ratio of the solid phase RSNO to the water uptake material ranges from 1:1 to 10:1.

13. The kit as defined in claim 12 wherein the device further comprises a solid phase additive to accelerate a rate of release of nitric oxide from the solid phase RSNO after exposure to water vapor, and wherein the solid phase additive is also completely sealed within the inner lumen of the housing.

14. The kit as defined in claim 13 wherein:
the solid phase additive is a component of the powder composition; and
the powder composition includes from about 40 wt % to about 85.5 wt % of the solid phase RSNO, from about 5 wt % to about 20 wt % of the solid phase additive, and from about 8 wt % to about 47.5 wt % of the water uptake material.

15. The kit as defined in claim 10 wherein:
the powder composition further comprises a solid phase additive to accelerate a rate of release of nitric oxide from the solid phase RSNO after exposure to water vapor; and
the solid phase additive is selected from the group consisting of zinc oxide nanoparticles, a copper (II/I) complex, copper nanoparticles, ascorbic acid, a thiol, a hydrogen ion precursor, a selenium species, an organoselenium molecule, an organo-tellurium species, stainless steel nanoparticles, gold nanoparticles, silica or polymeric particles coated with or possessing immobilized forms of an organic accelerant species, and combinations thereof.

16. The kit as defined in claim 15 wherein the powder composition consists of from about 15 wt % to about 95 wt % of the solid phase RSNO and from about 5 wt % to about 85 wt % of the solid phase additive.

17. The kit as defined in claim 10, further comprising a solid phase additive completely sealed within the inner lumen of the housing, wherein the solid phase additive is a metal wire.

18. The kit as defined in claim 10 wherein the polymeric wall is selected from the group consisting of silicone rubber, polyurethane, polyethylene, plasticized poly(vinyl chloride) (PVC), siloxane-based polyurethane elastomers, and thermoplastic silicone-polycarbonate-polyurethane.

19. The kit as defined in claim 10 wherein the catheter is an acute catheter or a chronic catheter.

20. The kit as defined in claim 19 wherein:
the acute catheter is selected from the group consisting of an intravascular catheter and a urinary catheter; or
the chronic catheter is selected from the group consisting of a tunneled dialysis catheter, a parenteral nutrition catheter, and a drug infusion catheter.

21. The kit as defined in claim 10 wherein the polymeric wall is an insert tube, and wherein the housing further comprises respective sealing mechanisms attached to opposed ends of the insert tube.

22. The kit as defined in claim 10 wherein an outer diameter of the catheter insert device ranges from about 0.5 mm to about 3 mm.

23. The kit as defined in claim 10 wherein:
a length of the insert housing is shorter than a length of the catheter;
a diameter of the insert housing is smaller than an inner diameter of the at least one lumen of the catheter tubing;
the length of the insert housing ranges from about 2 cm to about 20 cm; and
an outer diameter of the catheter insert device ranges from about 0.5 mm to about 3 mm.

24. The kit as defined in claim 10 wherein:
a length of the insert housing is shorter than a length of the adapter;
a diameter of the insert housing is smaller than an inner diameter of the adapter;
the length of the insert housing ranges from about 1 cm to about 5 cm; and
the diameter of the insert housing ranges from about 0.5 mm to about 3 mm.

25. A method, comprising:
locking a catheter insert device into place within a lumen of a catheter or within an adapter operatively connected to the catheter, whereby the catheter insert device is placed into contact with a lock solution in the lumen or within the adapter, the catheter insert device, including:
an insert housing, including a polymeric wall that is i) permeable to nitric oxide, ii) non-porous, and iii) permeable to water vapor; and
a powder composition completely sealed within the insert housing, the powder composition including a solid phase S-nitrosothiol (RSNO).

26. The method as defined in claim 25, further comprising allowing the catheter insert device to remain within the lumen of the catheter or within the adapter for a time period ranging from about 1 hour to about 3 days.

* * * * *